(12) United States Patent
Rubinstein et al.

(10) Patent No.: US 9,694,140 B2
(45) Date of Patent: *Jul. 4, 2017

(54) AUTOMATIC-LOCKING SAFETY NEEDLE COVERS AND METHODS OF USE AND MANUFACTURE

(71) Applicant: Sta-Med, LLC, Irvine, CA (US)

(72) Inventors: Sergio Rubinstein, Buffalo Grove, IL (US); Samuel Rosenberg, Orange Village, OH (US); Theodore Mosler, Raleigh, NC (US); Tianhong Ouyang, Cary, NC (US); David Foshee, Apex, NC (US)

(73) Assignee: Sta-Med, LLC, Irvine, CA (US)

( * ) Notice: Subject to any disclaimer, the term of this patent is extended or adjusted under 35 U.S.C. 154(b) by 574 days.

This patent is subject to a terminal disclaimer.

(21) Appl. No.: 14/287,728

(22) Filed: May 27, 2014

(65) Prior Publication Data

US 2014/0364803 A1    Dec. 11, 2014

Related U.S. Application Data

(63) Continuation of application No. 13/448,156, filed on Apr. 16, 2012, now Pat. No. 8,747,355, which is a
(Continued)

(51) Int. Cl.
*A61M 5/32*     (2006.01)
*A61M 5/42*     (2006.01)

(52) U.S. Cl.
CPC .......... *A61M 5/3245* (2013.01); *A61M 5/326* (2013.01); *A61M 5/3272* (2013.01);
(Continued)

(58) Field of Classification Search
CPC .. A61M 5/326; A61M 5/3272; A61M 5/3245; A61M 5/422; A61M 2005/3258; A61M 2005/3267; A61M 2005/3247
See application file for complete search history.

(56) References Cited

U.S. PATENT DOCUMENTS 2,460,641 A    2/1949 Kleiner
2,876,770 A    3/1959 White
(Continued)

FOREIGN PATENT DOCUMENTS

CN        103079610 B      6/2016
DE    20 2007 001717 U1    7/2007
(Continued)

OTHER PUBLICATIONS

BD Vacutainer® Passive Shielding Blood Collection Needle, BD Diagnostics, 2006, 4 pages.
(Continued)

*Primary Examiner* — Matthew F Desanto
(74) *Attorney, Agent, or Firm* — Knobbe, Martens, Olson & Bear, LLP

(57) ABSTRACT

A single-use needle cover configured to obscure, protect, or hide at least a portion of a needle from view before, during, and/or after an injection and/or aspiration procedure is disclosed. In some embodiments, the cover includes a housing at least partially containing the needle and configured to couple to a syringe, wherein the housing includes an axis and a guide member. In some embodiments, a sleeve has a plurality of tracks configured to slidingly receive the guide member, wherein the sleeve is configured to retract, extend, and rotate with respect to the housing. In some embodiments, after the sleeve has been retracted and extended one time, a first locking member inhibits further retraction of the sleeve and a second locking member inhibits rotation of the sleeve.

21 Claims, 39 Drawing Sheets

Related U.S. Application Data continuation of application No. 12/822,106, filed on Jun. 23, 2010, now Pat. No. 8,162,882.

(52) U.S. Cl.
CPC ..... *A61M 5/422* (2013.01); *A61M 2005/3247* (2013.01); *A61M 2005/3258* (2013.01); *A61M 2005/3267* (2013.01); *A61M 2205/59* (2013.01); *A61M 2207/00* (2013.01); *Y10T 29/49826* (2015.01); *Y10T 29/49863* (2015.01)

(56) References Cited

U.S. PATENT DOCUMENTS

| | | |
|---|---|---|
| 3,134,380 A | 5/1964 | Armao |
| 3,299,891 A | 1/1967 | Smeton |
| 3,757,780 A | 9/1973 | Ishikawa |
| 3,929,165 A | 12/1975 | Diebolt et al. |
| 4,127,131 A | 11/1978 | Vaillancourt |
| 4,180,071 A | 12/1979 | Oiwa |
| 4,205,675 A | 6/1980 | Vaillancourt |
| 4,273,123 A | 6/1981 | Lemelson |
| 4,276,170 A | 6/1981 | Vaillancourt |
| 4,316,462 A | 2/1982 | Baker |
| 4,318,402 A | 3/1982 | Vaillancourt |
| 4,326,569 A | 4/1982 | Vaillancourt |
| 4,349,035 A | 9/1982 | Thomas et al. |
| 4,365,626 A | 12/1982 | House |
| 4,416,290 A | 11/1983 | Lutkowski |
| 4,492,313 A | 1/1985 | Touzani |
| 4,511,359 A | 4/1985 | Vaillancourt |
| 4,525,157 A | 6/1985 | Vaillancourt |
| 4,525,374 A | 6/1985 | Vaillancourt |
| 4,585,435 A | 4/1986 | Vaillancourt |
| 4,610,683 A | 9/1986 | Vaillancourt |
| 4,617,012 A | 10/1986 | Vaillancourt |
| 4,636,200 A | 1/1987 | Vaillancourt |
| 4,636,313 A | 1/1987 | Vaillancourt |
| 4,645,495 A | 2/1987 | Vaillancourt |
| 4,652,256 A | 3/1987 | Vaillancourt |
| 4,655,750 A | 4/1987 | Vaillancourt |
| 4,678,462 A | 7/1987 | Vaillancourt |
| 4,682,607 A | 7/1987 | Vaillancourt |
| 4,702,739 A | 10/1987 | Milorad |
| 4,704,177 A | 11/1987 | Vaillancourt |
| 4,723,955 A | 2/1988 | Vaillancourt |
| 4,725,267 A | 2/1988 | Vaillancourt |
| 4,743,243 A | 5/1988 | Vaillancourt |
| 4,747,831 A | 5/1988 | Kulli |
| 4,773,458 A | 9/1988 | Touzani |
| 4,795,432 A | 1/1989 | Karczmer |
| 4,801,296 A | 1/1989 | Vaillancourt |
| 4,804,371 A | 2/1989 | Vaillancourt |
| 4,813,937 A | 3/1989 | Vaillancourt |
| 4,830,914 A | 5/1989 | Vaillancourt |
| 4,834,108 A | 5/1989 | Vaillancourt |
| 4,850,977 A | 7/1989 | Bayless |
| 4,850,996 A | 7/1989 | Cree |
| 4,863,431 A | 9/1989 | Vaillancourt |
| 4,867,743 A | 9/1989 | Vaillancourt |
| 4,887,998 A | 12/1989 | Martin et al. |
| 4,894,055 A | 1/1990 | Sudnak |
| 4,904,248 A | 2/1990 | Vaillancourt |
| 4,927,416 A | 5/1990 | Tomkiel |
| 4,935,016 A | 6/1990 | Deleo |
| 4,943,281 A | 7/1990 | Kothe |
| 4,971,068 A | 11/1990 | Sahi |
| 4,998,924 A | 3/1991 | Ranford |
| 5,011,479 A | 4/1991 | Le et al. |
| 5,015,240 A | 5/1991 | Soproni et al. |
| 5,026,356 A | 6/1991 | Smith |
| 5,057,086 A | 10/1991 | Dillard, III et al. |
| 5,059,185 A | 10/1991 | Ryan |
| 5,069,225 A | 12/1991 | Okamura |
| 5,080,648 A | 1/1992 | D'Antonio |
| 5,104,384 A | 4/1992 | Parry |
| 5,104,385 A | 4/1992 | Huband |
| 5,125,908 A | 6/1992 | Cohen |
| 5,156,599 A | 10/1992 | Ranford et al. |
| 5,180,370 A | 1/1993 | Gillespie |
| 5,222,502 A | 6/1993 | Kurose |
| 5,279,584 A | 1/1994 | Dillard, III et al. |
| 5,292,314 A | 3/1994 | D'Alessio et al. |
| 5,295,963 A | 3/1994 | Deeks |
| 5,295,975 A | 3/1994 | Lockwood, Jr. |
| 5,300,045 A | 4/1994 | Plassche, Jr. |
| 5,303,713 A | 4/1994 | Kurose |
| 5,308,332 A | 5/1994 | Dillard, III et al. |
| 5,312,370 A | 5/1994 | Talonn et al. |
| 5,336,187 A | 8/1994 | Terry et al. |
| 5,338,310 A | 8/1994 | Lewandowski |
| 5,348,544 A | 9/1994 | Sweeney et al. |
| 5,360,409 A | 11/1994 | Boyd, III et al. |
| 5,364,372 A | 11/1994 | Danks et al. |
| 5,368,568 A | 11/1994 | Pitts et al. |
| 5,389,085 A | 2/1995 | D'Alessio et al. |
| 5,403,286 A | 4/1995 | Lockwood, Jr. |
| 5,415,645 A | 5/1995 | Friend et al. |
| 5,423,765 A | 6/1995 | Hollister |
| 5,462,533 A | 10/1995 | Daugherty |
| 5,472,430 A | 12/1995 | Vaillancourt |
| 5,514,116 A | 5/1996 | Vaillancourt |
| 5,520,193 A | 5/1996 | Suzuki et al. |
| 5,578,011 A | 11/1996 | Shaw |
| 5,582,597 A | 12/1996 | Brimhall et al. |
| 5,601,536 A | 2/1997 | Crawford et al. |
| 5,609,577 A | 3/1997 | Haber et al. |
| 5,632,733 A | 5/1997 | Shaw |
| 5,651,480 A | 7/1997 | Piepenstock |
| 5,656,031 A | 8/1997 | Thorne et al. |
| 5,674,203 A | 10/1997 | Lewandowski |
| 5,688,241 A | 11/1997 | Asbaghi |
| 5,735,823 A | 4/1998 | Berger |
| 5,746,727 A | 5/1998 | Graves |
| 5,795,336 A | 8/1998 | Romano et al. |
| 5,823,973 A | 10/1998 | Racchini et al. |
| 5,824,001 A | 10/1998 | Erskine |
| 5,879,337 A | 3/1999 | Kuracina et al. |
| 5,893,845 A | 4/1999 | Newby et al. |
| 5,935,104 A | 8/1999 | Janek et al. |
| 5,964,739 A | 10/1999 | Champ |
| 5,976,111 A | 11/1999 | Hart |
| 5,984,899 A | 11/1999 | D'Alessio et al. |
| 6,042,570 A | 3/2000 | Bell et al. |
| 6,090,077 A | 7/2000 | Shaw |
| RE36,885 E | 9/2000 | Blecher et al. |
| 6,186,980 B1 | 2/2001 | Brunel |
| 6,203,529 B1 | 3/2001 | Gabriel et al. |
| 6,287,278 B1 | 9/2001 | Woehr et al. |
| 6,302,868 B1 | 10/2001 | Mohammad |
| 6,379,336 B1 | 4/2002 | Asbaghi |
| 6,468,383 B2 | 10/2002 | Kundel |
| 6,524,279 B1 | 2/2003 | Shields |
| 6,572,584 B1 | 6/2003 | Shaw et al. |
| 6,623,458 B2 | 9/2003 | Woehr et al. |
| 6,629,959 B2 | 10/2003 | Kuracina et al. |
| 6,648,856 B1 | 11/2003 | Argento |
| 6,648,858 B2 | 11/2003 | Asbaghi |
| 6,679,864 B2 | 1/2004 | Gagnieux et al. |
| 6,699,221 B2 | 3/2004 | Vaillancourt |
| 6,706,000 B2 | 3/2004 | Perez et al. |
| 6,712,792 B2 | 3/2004 | Leong |
| 6,719,730 B2 | 4/2004 | Jansen et al. |
| 6,733,465 B1 | 5/2004 | Smutney et al. |
| 6,749,588 B1 | 6/2004 | Howell et al. |
| 6,761,706 B2 | 7/2004 | Vaillancourt |
| 6,776,775 B1 | 8/2004 | Mohammad |
| 6,796,967 B2 | 9/2004 | Jensen |
| 6,808,507 B2 | 10/2004 | Roser |
| 6,855,129 B2 | 2/2005 | Jensen et al. |
| 6,860,871 B2 | 3/2005 | Kuracina et al. |
| 6,869,415 B2 | 3/2005 | Asbaghi |
| 6,872,190 B1 | 3/2005 | Denis et al. |
| 6,905,483 B2 | 6/2005 | Newby et al. |

(56) References Cited

U.S. PATENT DOCUMENTS

| | | |
|---|---|---|
| 6,926,697 B2 | 8/2005 | Malenchek |
| 6,958,055 B2 | 10/2005 | Donnan et al. |
| 6,966,898 B1 | 11/2005 | Pouget et al. |
| 6,984,223 B2 | 1/2006 | Newby et al. |
| 6,986,760 B2 | 1/2006 | Giambattista et al. |
| 6,997,913 B2 | 2/2006 | Wilkinson |
| 7,037,294 B2 | 5/2006 | Luther et al. |
| 7,083,600 B2 | 8/2006 | Meloul |
| 7,101,351 B2 | 9/2006 | Crawford et al. |
| 7,160,267 B2 | 1/2007 | Brown |
| 7,186,239 B2 | 3/2007 | Woehr |
| 7,198,617 B2 | 4/2007 | Millerd |
| 7,201,740 B2 | 4/2007 | Crawford |
| 7,226,432 B2 | 6/2007 | Brown |
| 7,306,566 B2 | 12/2007 | Raybuck |
| 7,306,740 B2 | 12/2007 | Freund |
| 7,314,464 B2 | 1/2008 | Giambattista et al. |
| 7,354,422 B2 | 4/2008 | Riesenberger et al. |
| 7,357,783 B2 | 4/2008 | Millerd |
| 7,361,160 B2 | 4/2008 | Hommann et al. |
| 7,396,343 B2 | 7/2008 | Brown |
| 7,469,458 B1 | 12/2008 | Starnes |
| 7,524,308 B2 | 4/2009 | Conway |
| 7,530,967 B2 | 5/2009 | Brown |
| 7,615,033 B2 | 11/2009 | Leong |
| 7,632,243 B2 | 12/2009 | Bialecki et al. |
| 7,648,480 B2 | 1/2010 | Bosel et al. |
| 7,666,164 B2 | 2/2010 | Giambattista et al. |
| 7,678,077 B2 | 3/2010 | Harris et al. |
| 7,736,322 B2 | 6/2010 | Roe et al. |
| 7,766,879 B2 | 8/2010 | Tan et al. |
| D623,732 S | 9/2010 | Brady et al. |
| 7,811,261 B2 | 10/2010 | Rubinstein et al. |
| 7,815,611 B2 | 10/2010 | Brown |
| 7,828,817 B2 | 11/2010 | Belef et al. |
| 7,922,698 B2 | 4/2011 | Riesenberger et al. |
| 7,927,314 B2 | 4/2011 | Kuracina et al. |
| 8,002,751 B2 | 8/2011 | Carr |
| 8,162,882 B2 * | 4/2012 | Rubinstein ............ A61M 5/326 604/110 |
| 8,177,745 B2 | 5/2012 | Brechbuehler et al. |
| RE43,473 E | 6/2012 | Newby et al. |
| 8,211,036 B2 | 7/2012 | Schraga |
| 8,308,691 B2 | 11/2012 | Woehr et al. |
| 8,419,688 B2 | 4/2013 | Woehr et al. |
| 8,435,738 B2 | 5/2013 | Holmes |
| 8,460,247 B2 | 6/2013 | Woehr et al. |
| 8,475,739 B2 | 7/2013 | Holmes et al. |
| 8,486,027 B2 | 7/2013 | Findlay et al. |
| 8,568,367 B2 | 10/2013 | Griffiths et al. |
| 8,663,129 B2 | 3/2014 | Allen et al. |
| 8,747,355 B2 * | 6/2014 | Rubinstein ............ A61M 5/326 604/110 |
| 9,445,760 B2 | 9/2016 | Allen et al. |
| 2002/0004649 A1 | 1/2002 | Jansen et al. |
| 2003/0040717 A1 | 2/2003 | Saulenas et al. |
| 2003/0050608 A1 | 3/2003 | Brown |
| 2003/0078548 A1 | 4/2003 | Kobayashi |
| 2003/0114797 A1 | 6/2003 | Vaillancourt |
| 2003/0144632 A1 | 7/2003 | Hommann et al. |
| 2003/0212369 A1 | 11/2003 | Kobayashi |
| 2004/0087914 A1 | 5/2004 | Bryan et al. |
| 2004/0112457 A1 | 6/2004 | Norton et al. |
| 2004/0204662 A1 | 10/2004 | Perez et al. |
| 2004/0210197 A1 | 10/2004 | Conway |
| 2004/0222579 A1 | 11/2004 | Adoline et al. |
| 2004/0254499 A1 | 12/2004 | Smutney et al. |
| 2005/0113750 A1 | 5/2005 | Targell |
| 2005/0267410 A1 | 12/2005 | Koska |
| 2005/0277893 A1 | 12/2005 | Liversidge |
| 2006/0079847 A1 | 4/2006 | Crawford |
| 2006/0189933 A1 * | 8/2006 | Alheidt ................ A61M 5/326 604/110 |
| 2006/0224122 A1 | 10/2006 | Bosel et al. |
| 2006/0229570 A1 | 10/2006 | Lovell et al. |
| 2007/0060893 A1 | 3/2007 | Mahurkar |
| 2007/0129683 A1 | 6/2007 | Brungardt |
| 2007/0179451 A1 | 8/2007 | Sprinkle et al. |
| 2007/0265566 A1 | 11/2007 | Simpson |
| 2007/0293819 A1 | 12/2007 | Giambattista et al. |
| 2008/0097353 A1 | 4/2008 | Carr |
| 2008/0319346 A1 | 12/2008 | Crawford et al. |
| 2009/0177167 A1 | 7/2009 | Kuracina et al. |
| 2009/0204026 A1 | 8/2009 | Crawford et al. |
| 2009/0227950 A1 | 9/2009 | Jensen et al. |
| 2009/0227956 A1 | 9/2009 | Emmott et al. |
| 2010/0004602 A1 | 1/2010 | Nord et al. |
| 2010/0010372 A1 | 1/2010 | Brown et al. |
| 2010/0042053 A1 | 2/2010 | Dillard, III |
| 2010/0087784 A1 | 4/2010 | Bosel et al. |
| 2010/0160865 A1 | 6/2010 | Zeltzer et al. |
| 2010/0262038 A1 | 10/2010 | Tan et al. |
| 2010/0280488 A1 | 11/2010 | Pruitt et al. |
| 2010/0286558 A1 | 11/2010 | Schraga |
| 2010/0298770 A1 | 11/2010 | Rubinstein et al. |
| 2011/0077600 A1 | 3/2011 | Uchida et al. |
| 2011/0106148 A1 | 5/2011 | Ginn et al. |
| 2011/0152832 A1 | 6/2011 | Foshee et al. |
| 2011/0257603 A1 | 10/2011 | Ruan et al. |
| 2011/0270198 A1 | 11/2011 | Perot et al. |
| 2011/0276014 A1 | 11/2011 | Saitoh et al. |
| 2012/0071790 A1 | 3/2012 | Schraga |
| 2012/0277628 A1 | 11/2012 | Schraga |
| 2014/0135706 A1 | 5/2014 | Rubinstein et al. |
| 2014/0236046 A1 | 8/2014 | Allen et al. |

FOREIGN PATENT DOCUMENTS

| | | |
|---|---|---|
| EP | 0250104 A1 | 12/1987 |
| EP | 0329038 B1 | 2/1993 |
| EP | 2298394 A1 | 3/2011 |
| FR | 2930160 | * 10/2009 |
| GB | 732 313 | 6/1955 |
| JP | 6009440 | 9/2016 |
| WO | WO 02/09797 | 2/2002 |
| WO | WO 02/083205 | 10/2002 |
| WO | WO 03/066141 | 8/2003 |
| WO | WO 2004/069301 | 8/2004 |
| WO | WO 2004/069302 | 8/2004 |
| WO | WO 2004/110535 | 12/2004 |
| WO | WO 2006/029003 A2 | 3/2006 |
| WO | WO 2008/077706 A1 | 7/2008 |
| WO | WO 2009/039022 A2 | 3/2009 |
| WO | WO 2009/148969 | 12/2009 |
| WO | WO 2009/154131 A1 | 12/2009 |
| WO | WO 2010/019201 A1 | 2/2010 |
| WO | WO 2010/019936 A1 | 2/2010 |
| WO | WO 2011/162913 A1 | 12/2011 |
| WO | WO 2012/166746 A1 | 12/2012 |

OTHER PUBLICATIONS

Injectable Drug Delivery 2010: Devices Focus, ONdrugDelivery Series, Aug. 2010, www.ondrugdelivery.com.

Introducing the 8 mm and 5 mm BD Autoshield™ Pen Needles, May 2009, 2 pages.

Smiths Medical, "Smiths Medical Wins $30 Million in Contracts for Safety Devices", Paul Harris—Director Communications, available online at: <http://www.smiths-medical.com/plugins/news/2008/may/30-million-contract.html>, May 29, 2008.

Stoker, Ron, "Stuck at Work Use Safety Blood Draw Products to Avoid Needlestick Injuries," Managing Infection Control, Jan. 2007, 6 pages.

Letter from Mark W. Godfrey to Dave Allen, dated Sep. 28, 2010, 2 pages.

Docket for Case No. Case No. 30-2011 00467970: *Mark W. Godfrey and Stephen M. Jokela v. Sta-Med, LLC and Russell R. Stepke*, in 6 pages.

Excerpts of First Amended Complaint for: (1) Breach of Oral Agreement [by Mark W. Godfrey]; (2) Breach of Oral Agreement [by Stephen E. Jokela]; (3) Breach of Written Contract [by Mark W.

(56) References Cited

OTHER PUBLICATIONS

Godfrey]; (4) Breach of Written Contract [by Mark W. Godfrey]; (5) Breach of Implied Covenant of Good Faith and Fair Dealing; (6) Labor Code Violation [§ 218.5]; (7) Declaratory Relief; (8) Breach of Fiduciary Duty; (9) Promissory Estoppel; (10) Promissory Fraud; and (11) Conversion, in Case No. 30-2011 00467970: *Mark W. Godfrey and Stephen M. Jokela* v. *Sta-Med, LLC and Russell R. Stepke*, dated Apr. 4, 2012, in 9 pages.

Excerpts of Cross-Complaint Against Mark W. Godfrey and Stephen M. Jokela, in Case No. 30-2011 00467970: *Mark W. Godfrey and Stephen M. Jokela* v. *Sta-Med, LLC and Russell R. Stepke*, dated May 31, 2011, in 2 pages.

Excerpts of Mark W. Godfrey's Responses to Sta-Med, LLC's Request for Admissions of Documents (Set No. One), in Case No. 30-2011 00467970: *Mark W. Godfrey and Stephen M. Jokela* v. *Sta-Med, LLC and Russell R. Stepke*, dated Sep. 14, 2011, in 4 pages.

Excerpts of Mark W. Godfrey's Responses to Sta-Med, LLC's Form Interrogatories (Set No. One), in Case No. 30-2011 00467970: *Mark W. Godfrey and Stephen M. Jokela* v. *Sta-Med, LLC and Russell R. Stepke*, dated Sep. 21, 2011, in 17 pages.

Excerpts of Transcript of Deposition of Stephen M. Jokela, vol. 1, in Case No. 30-2011 00467970: *Mark W. Godfrey and Stephen M. Jokela* v. *Sta-Med, LLC and Russell R. Stepke*, Jul. 11, 2011, in 8 pages.

Excerpts of Transcript of Deposition of Theodore Mosler, in Case No. 30-2011 00467970: *Mark W. Godfrey and Stephen M. Jokela* v. *Sta-Med, LLC and Russell R. Stepke*, Oct. 26, 2011, in 17 pages.

Excerpts of Transcript of Deposition of Todd Korogi, in Case No. 30-2011 00467970: *Mark W. Godfrey and Stephen M. Jokela* v. *Sta-Med, LLC and Russell R. Stepke*, Oct. 26, 2011, in 2 pages.

International Search Report and Written Opinion in International Application No. PCT/US2011/038440, mailed Oct. 21, 2011, in 10 pages.

International Preliminary Report on Patentability in International Application No. PCT/US2011/038440, issued Dec. 28, 2012, in 7 pages.

Communication pursuant to Rules 161(1) and 162 EPC in corresponding European Application No. 11724893.0, dated Feb. 15, 2013, in 2 pages.

Office Action in corresponding Chinese Application No. 201180040577.X, dated May 4, 2014, in 19 pages.

Office Action in related Chinese Application No. 201180040577.X, dated Feb. 11, 2015, in 8 pages.

Office Action in related Chinese Application No. 201180040577.X, dated May 21, 2015, in 5 pages.

Office Action in related Chinese Application No. 201180040577.X, dated Sep. 14, 2015, in 8 pages.

Office Action in related Japanese Application No. 2013-516583, mailed Mar. 16, 2015, in 10 pages.

Office Action in related Japanese Application No. 2013-516583, mailed Jan. 4, 2016, in 10 pages.

\* cited by examiner

AUTOMATIC-LOCKING SAFETY NEEDLE COVERS AND METHODS OF USE AND MANUFACTURE

CROSS REFERENCE TO RELATED APPLICATIONS

This application is a continuation of U.S. application Ser. No. 13/448,156, filed Apr. 16, 2012, titled "AUTOMATIC-LOCKING SAFETY NEEDLE COVERS AND METHODS OF USE AND MANUFACTURE," which is a continuation of U.S. application Ser. No. 12/822,106, filed Jun. 23, 2010, now U.S. Pat. No. 8,162,882, titled "AUTOMATIC-LOCKING SAFETY NEEDLE COVERS AND METHODS OF USE AND MANUFACTURE," the entirety of each of which is incorporated herein by reference.

BACKGROUND

Certain embodiments disclosed herein relate to needle covers and needle cover assemblies for medical devices, such as syringes, and are particularly related to obscuring at least a portion of the needle from view and aiding in the transfer of fluids.

DESCRIPTION OF THE RELATED ART

Syringes are used throughout the medical industry for the injection and withdrawal of a wide variety of fluids and solutions into and from the human body. Due to the numerous potential hazards associated with the handling and manipulation of bodily fluids, and particularly blood, there are a number of known safety features that are frequently incorporated into various types of syringes and syringe needles. For example, many syringe needles are provided with a removable cap that generally prevents needle sticks while the cover is in place. When the cap is removed, the needle is exposed. These caps are removed before an injection and/or aspiration procedure and replaced after the injection and/or aspiration procedure before discarding the needle. Among other concerns, this removal and replacement procedure creates a risk of accidental needle sticks.

Syringes and syringe needles are frequently configured such that at least the needles are disposable; that is, they are intended to be used only once and then thrown away. This procedure reduces the likelihood of transferring blood or tissue-born diseases from one patient to another. To this end, many syringe needles are configured to be quickly and easily detached from an appropriately configured syringe body. In this way, the syringe body may be reusable, and made of a relatively durable material, such as metal, while the disposable needle assemblies may be made of plastic or other similar, relatively inexpensive, materials.

SUMMARY

Several variations and combinations of needle covers are disclosed. In certain embodiments a single-use needle cover comprises a housing configured to couple to a syringe and at least partly (or completely) contain or shield from view the needle, wherein the housing includes a guide member, a first locking member, and a second locking member; a sleeve configured to move or telescope between an extended position and a retracted position with respect to the housing, wherein the extended position generally covers a distal tip of the needle and the retracted position exposes at least a portion of the distal tip of the needle, and wherein the sleeve is biased toward the extended position. In some embodiments, the movement or telescoping of the sleeve from the extended position to the retracted position rotates the sleeve with respect to the housing, transfers the guide member from a first track to a second track included in the sleeve, and engages a first locking member; wherein movement or telescoping of the sleeve from the retracted position to the extended position engages a second locking member; and wherein the first and second locking members inhibit movement or telescoping of the cover to prevent reuse. In some arrangements, the first locking member comprises a rib on the housing. In some embodiments, the second locking member comprises a radially inwardly extending arm on the housing. In some embodiments, the sleeve further includes a flange, which engages the first and second locking members. In some arrangements, the first locking member comprises a rib on the housing, the second locking member comprises a radially inwardly extending arm on the housing, and the sleeve further includes a flange that engages the first and second locking members. In some embodiments, the sleeve includes a third track intersecting the first and second tracks. The third track can intersect the first track proximal to the intersection of the third track and the second track.

According to certain arrangements, a single-use needle cover can comprise: a housing at least partially containing the needle and configured to couple to a syringe, wherein the housing includes an axis and a guide member; a sleeve configured to receive a distal tip of the needle and to translate between a first position and a second position, wherein the sleeve rotates with respect to the housing during at least some of the translation, wherein the sleeve includes a plurality of tracks configured to receive the guide member; and wherein translation of the sleeve engages a first locking member configured to inhibit reuse of the needle cover. In some embodiments, the first position covers the distal tip of the needle and the second position exposes the distal tip of the needle. In the cover, the first locking member can inhibit reuse of the needle cover by inhibiting translation of the sleeve. The translation of the sleeve can also engage a second locking member configured to inhibit reuse of the needle cover. The second locking member can inhibit reuse of the needle cover by inhibiting rotation of the sleeve. In some embodiments, the first locking member is an arm coupled to the housing and the second locking member is a rib coupled to the housing. A spring can bias the sleeve toward the first position. In some embodiments, the sleeve can translate from the first position to the second position substantially without impediment. The sleeve can include a flange configured to engage the first locking member. The flange can be further configured to engage a second locking member. The first locking member can be engaged as the sleeve translates from the first position to the second position. A second locking member can be engaged as the sleeve translates from the second position to the first position.

According to certain embodiments a method of manufacturing a single-use needle cover can comprise: forming a housing, wherein the housing at least partially contains the needle is and configured to couple to a syringe, wherein the housing includes an axis and a guide member; forming a sleeve, wherein the sleeve is configured to receive a distal tip of the needle and to translate between a first position and a second position, wherein the sleeve rotates with respect to the housing during at least some of the translation, wherein the sleeve includes a plurality of tracks configured to receive the guide member; and wherein translation of the sleeve engages a first locking member configured to inhibit reuse of the needle cover. In some methods, the first position can cover the distal tip of the needle and the second position can expose the distal tip of the needle. The first locking member can inhibit reuse of the needle cover by inhibiting translation of the sleeve. The translation of the sleeve can also engage a second locking member configured to inhibit reuse of the needle cover. The second locking member can inhibit reuse of the needle cover by inhibiting rotation of the sleeve.

In certain arrangements, a method of protecting against unintentional needle sticks with a needle cover can comprise: forming a housing, wherein the housing at least partially contains the needle is and configured to couple to a syringe, wherein the housing includes an axis and a guide member; forming a sleeve, wherein the sleeve includes a plurality of tracks configured to receive the guide member, wherein the sleeve is configured to receive a distal tip of the needle and to move between a first position and a second position, wherein the first position covers the distal tip of the needle and the second position exposes the distal tip of the needle, and wherein the sleeve rotates with respect to the housing during at least some of the movement; and wherein movement of the sleeve engages a first locking member configured to inhibit further movement of the sleeve. In some embodiments, the first locking member inhibits reuse of the needle cover by inhibiting rotation of the sleeve. In some embodiments the first locking member inhibits reuse of the needle cover by axial movement of the sleeve. The movement of the sleeve can further engage a second locking member configured to inhibit reuse of the needle cover. In some embodiments, the second locking member inhibits reuse of the needle cover by inhibiting axial movement of the sleeve. In some embodiments, the second locking member inhibits reuse of the needle cover by inhibiting rotation of the sleeve.

DETAILED DESCRIPTION OF PREFERRED EMBODIMENTS

A variety of examples of needle covers are described below to illustrate various examples that may be employed to achieve the desired improvements. These examples are only illustrative and not intended in any way to restrict the general inventions presented and the various aspects and features of these inventions. For example, although embodiments and examples are provided herein in the medical field, the inventions are not confined exclusively to the medical field and certain embodiments can be used in other fields.

Furthermore, the phraseology and terminology used herein is for the purpose of description and should not be regarded as limiting. No features, structure, or step disclosed herein is essential or indispensible.

Figure 1:
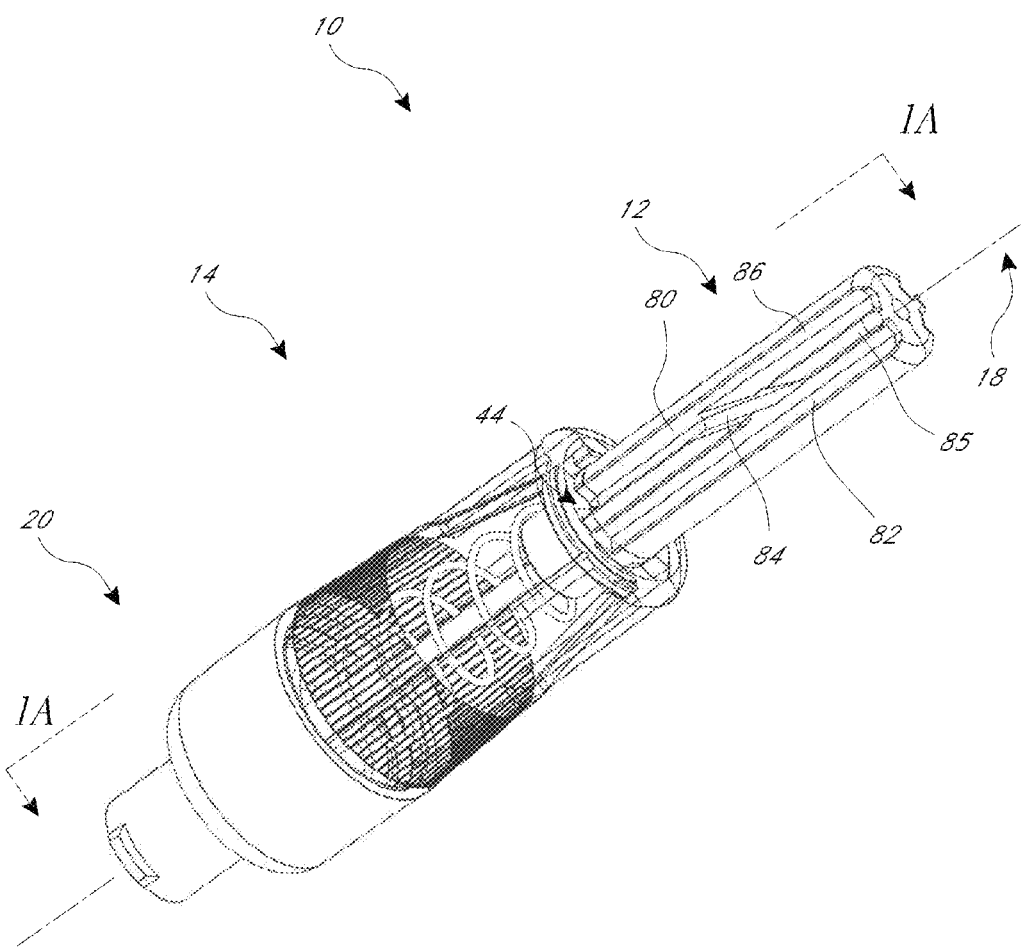
FIG. 1 illustrates a perspective view of an embodiment of a needle cover.

FIG. 1 illustrates a needle cover 10 that may be removably coupled to a standard or specially configured syringe (not shown). The cover 10 includes features and components, discussed below in detail, that generally obscure, protect, or hide at least a portion of (or substantially all of) a needle 16 from view before, during, and/or after an injection and/or aspiration procedure, thereby reducing or alleviating at least some anxiety or fear that might otherwise be felt by certain patients or other individuals upon seeing the needle 16. In some embodiments, all or nearly all of the needle is obscured, hidden, or protected by the cover 10. The cover 10 can also include features and components that permit a fluid transfer procedure to be performed before an injection and/or aspiration procedure without automatically preventing further use, but that automatically prevent the cover 10 and the associated needle 16 from being used more than once to perform an injection and/or aspiration procedure. As used herein, the terms "automatically," and "automatic," and similar terms, are intended to have their ordinary meanings in the field. In some embodiments, as the context reflects, these terms refer to a mechanism or process that occurs in normal usage of a product, or that occurs while the user is performing another process, without requiring an additional step or manipulation by the user to achieve the desired result. Although the illustrated cover 10 is configured to be coupled to and removed from a syringe, the cover 10 may instead be integrally formed with the syringe or connected, either removably or permanently, to another medical implement. In either case, the syringe is generally of a known type suitable for the withdrawal and injection and/or aspiration of fluids or other solutions by way of the cover 10. The locking system and/or reuse-inhibition features of the cover 10 could be used with many different types of medical and non-medical products.

Figure 1A:
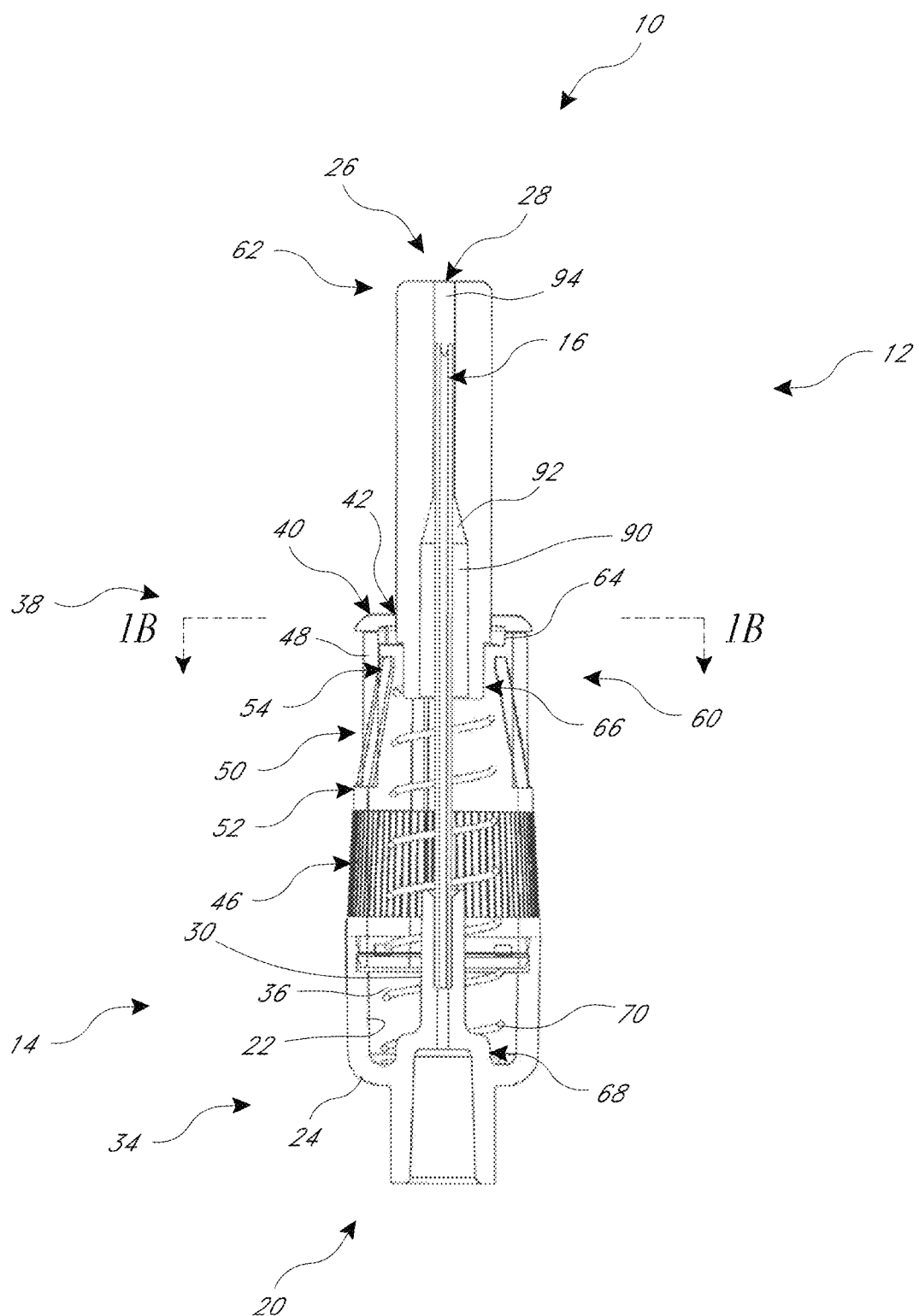
FIG. 1A illustrates a cross-sectional view of the embodiment of FIG. 1 along the line 1A-1A in a ready for use, fully extended and unlocked, first position.

In the illustrated construction of FIGS. 1 and 1A, the cover 10 includes a generally cylindrical housing 14 that includes an axis 18, along which the needle 16 is positioned. A distal end of the housing 14 couples to a sleeve 12 configured to move along and at least partially rotate about the axis 18. As used herein, "proximal," or any derivative thereof, refers to a direction toward the end of the cover 10 that connects to a medical device, e.g. a syringe; "distal," or any derivatives thereof, refers to a direction toward the end of the cover 10 that contacts the surface to be penetrated with the needle 16, e.g. a patient's skin. A channel 26 and an aperture 28 are included in the sleeve 12 in order to permit the needle 16 to pass therethrough.

In some embodiments, a proximal end 34 of the housing 14 can comprise a hub 20 that can be configured for either removable or permanent attachment to the syringe, or that may be integrally formed with the syringe. For example, the hub 20 may include internal or external threads or other suitable coupling, latching, or locking features such as tabs, slots, projections, pressure/snap fits, and the like, which may be provided in various combinations on various portions of the hub 20 for coupling to the syringe. The coupling features can engage corresponding features provided on the syringe to removably couple the cover 10 to the syringe. In some embodiments, the hub 20 may be permanently fixed (e.g. by sonic welding, adhesive, pressure/snap fit, or the like) or integrally formed with the syringe. In some embodiments, the housing 14 includes a generally cylindrically reduced needle support portion 30 that extends axially from the hub 20 and supports the needle 16. As shown, the housing 14 and/or hub 20 are in fluid communication with the needle 16, thus permitting fluid to pass between the syringe and the needle 16.

The inside surface 22 of the housing 14 can include a central chamber 36. A distal end 38 of the housing 14 can include a radially inwardly extending shoulder 40 that includes an opening 42 that communicates with the chamber 36. The opening 42 slidingly receives the sleeve 12 that in turn receives and at least partially covers the needle 16, as will be discussed in further detail below. A guide member 44 extends radially inwardly from the shoulder 40 and is configured to engage one or more tracks formed in the sleeve 12. The outer surface 24 of the housing 14 can include an outer portion 46 that is textured, knurled, or the like to facilitate grasping the cover 10.

As shown in FIGS. 1 and 1A, the housing 14 can include at least one axial locking member 50. In some embodiments the axial locking member 50 is positioned at least partially within an opening 48 included in the housing 14. As shown, a first end 52 of the axial locking member 50 can be coupled to the housing 14, while the second end 54 of the axial locking member 50 can be disposed radially inward compared to the inner surface 22. In some embodiments, the axial locking member 50 is generally resilient, so that the radially inwardly disposed second ends 54 can flex and then return to the original position even after the ends 54 have been radially outwardly deflected. In some embodiments, the first end 52 is larger than the second end 54, e.g. the axial locking member 50 can taper from the first end 50 to the second end 54. In some embodiments, the axial locking member 50 includes a latching member, such as a hook, clasp, detent, ratchet, or other structure.

In the illustrated arrangement the housing 14 is of unitary construction. This can be advantageous in that it reduces the total number of components to be assembled to form the cover 10. In some embodiments, the housing 14 is formed from a plurality of components. For example, a proximal portion and a distal portion of the housing 14 can be separate components that are joined using techniques, such as but not limited to sonic welding, adhesive, snap or press fitting, or the like.

With regard to FIG. 1A, the illustrated sleeve 12 includes a proximal end 60 positioned within the chamber 36 and a distal end 62 generally covering the distal tip 96 of the needle 16. The proximal end 60 includes a radially outwardly extending flange 64 that seats against the shoulder 40 of the distal end 38. As shown, the proximal end 60 can also include a substantially annular and axially extending locating portion 66 that locates a biasing member in the form of a spring 70. In some embodiments the inner surface 22 of the proximal end 34 of the housing 14 includes a similar portion 68 for locating the spring 70. The sleeve 12 can include a collapsible portion.

In the illustrated embodiment, the spring 70 engages and extends between the proximal end 60 of the sleeve 12 and the proximal end 34 of the housing 14. The spring 70 biases the sleeve 12 toward an extended position in which the flange 64 of the sleeve 12 is biased into engagement with the shoulder 40 of the distal end of the housing 38, and the sleeve 12 completely covers the distal tip 96 of the needle 16. Many types of springs may be employed, such as but not limited to a helical coil spring, conical spring, wave-spring, Belleville washer, or the like. In some embodiments, the spring 70 is a helical coil spring having a free length of about 25 mm and a spring rate of about 0.12 N/mm through the linear portion of the spring's deflection. Other constructions may include softer or stiffer springs depending on the application, and may be constructed of substantially any suitable material. In some embodiments, the spring 70 is configured to facilitate retraction of the sleeve 12 by a user applying distal pressure to the syringe and/or the cover 10 with just one hand. Progressive springs and/or multiple springs of varying lengths may also be used to provide a variable effective spring rate during movement of the sleeve 12 between fully extended and fully retracted positions.

The channel 26 can extend through the sleeve 12 and include a proximal portion 90, a tapered portion 92, and a distal portion 94. The proximal portion 90 can be configured to receive the needle support portion 30 of the housing 14 as the sleeve 12 is retracted. For example, in some embodiments the needle support portion 30 has a diameter of at least about 0.5 mm and/or less than or equal to about 5 mm and an axial length of at least about 2 mm and/or less than or equal to about 2.5 mm and the proximal portion 90 of the channel 26 has a diameter of at least about 0.6 mm, and/or less than or equal to about 6 mm and an axial length of at least about 2.5 mm and/or less than or equal to about 26 mm. In some embodiments, the diameter of the proximal portion 90 is larger than the diameter of the distal portion 92. In the arrangement shown, the tapered portion 92 transitions between the proximal and distal channel portions 90, 94. The tapered portion 92 can guide the needle 16 into the distal channel 94. In the embodiment shown, the distal portion 94 of the channel 26 has a diameter that is about the same as the outside diameter of the needle 16 in order to, for example, support the needle 16.

Figure 1B:
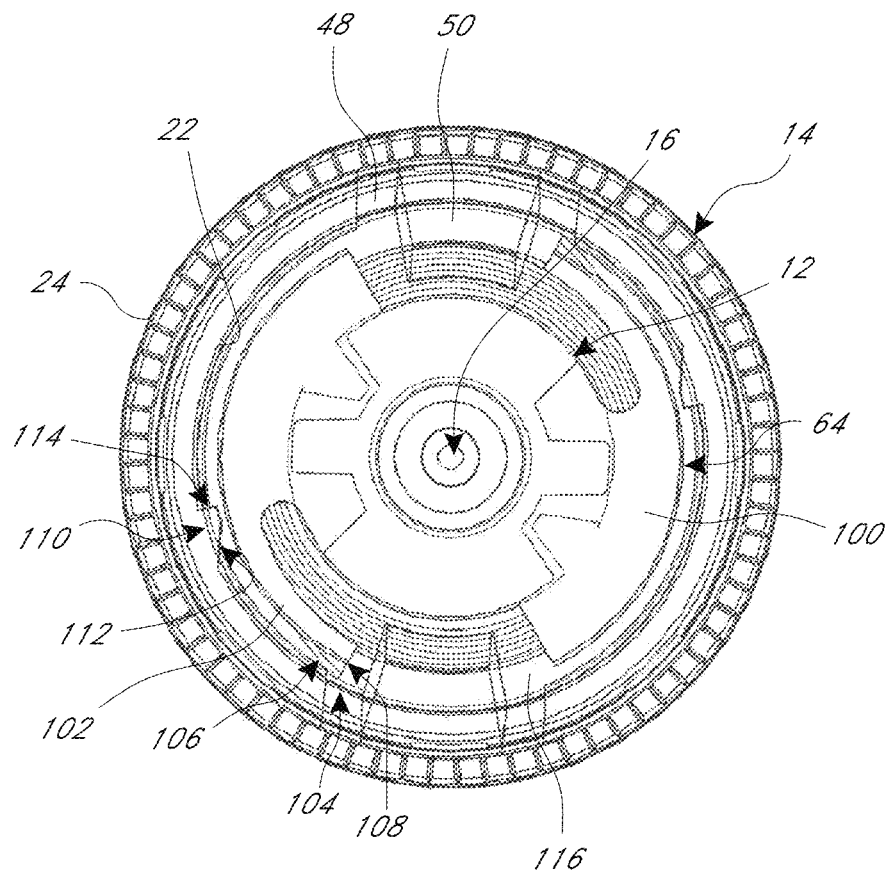
FIG. 1B illustrates a cross-sectional view along the line 1B-1B.

Turning now to FIG. 1B, the illustrated flange 64 includes an outwardly extending portion 100 from which an impeding member 102, such as a resilient member, extends, e.g. circumferentially, radially, axially, a combination thereof, or the like. The end 104 of the impeding member 102 shown is shaped as a radially outwardly extending wedge (such that the radial width of the impeding member 102 increases toward the end 104) that has an inclined face 106 and a generally flat face 108. Similarly, a generally wedge-shaped rotational locking member 110, e.g. an axial rib, extends radially inwardly from the inner surface 22 of the housing 14 and includes an inclined face 112 and a generally flat face 114. In the variant shown, the inclined face 112 is configured to be in the opposite direction as the inclined face 106. Although the end 104 and rotational locking member 110 shown are generally wedge-shaped, many shapes can be used, such as but not limited to generally hemispherical, frustoconical, undulating or the like. In some embodiments, the axial length of the rotational locking member 110 is greater than the axial length of the impeding member 102 and/or the sleeve 64. In some embodiments, at least a portion of the impeding member 102 is configured to fit into at least a portion of the rotational locking member 110 or vice versa. For example, the impeding member 102 can comprise a tab configured to fit within a slot included in the rotational locking member 110. In some embodiments, at least a portion of the impeding member 102 is configured to fit into an opening in the housing 14. A notch 116 separates the outwardly extending portion 100 and the end 104. The notch 116 can be configured to be at least as large as the axial cross-section of the axial locking member 50, as will be discussed in further detail below.

Turning back to FIG. 1, the sleeve 12 includes a plurality of tracks 80-84 to aid in, for example, directing the sleeve 12 during movement. In many arrangements, the tracks are configured to slidingly receive the guide member 44 of the housing 12. Accordingly, the tracks 80-84 can be configured to have a similar cross-sectional shape as the guide member 44, e.g., generally rectangular, generally T-shaped, generally circular sector, or the like. For instance, the illustrated guide member 44 and the tracks 80-84 are generally trapezoidal in cross sectional shape. A first track 80 and a second track 82 are generally parallel to the axis 18 and extend along the sleeve 12 from the proximal end 60 to the distal end 62. A separation member 85 separates the tracks 80, 82 throughout at least a portion of, or most of, their length. A separate transfer track 84 can be positioned in a middle or intermediate region along the length of the sleeve and at angle relative to the axis 18 (e.g., non-parallel to the axis), and can interrupt the separation member 85 and intersect the first and second tracks 80, 82. The transfer track 84 can thus connect the first and second tracks 80, 82 to permit the guide member 44 to shift between the first and second tracks 80, 82 as will be discussed in further detail below. The transfer track 84 can be generally straight and non-curvilinear to facilitate smooth travel along the transfer tack 84. In the example illustrated, the intersection of the transfer track 84 is positioned in about the middle of the sleeve 12, and the intersection of the transfer track 84 and the first track 80 is proximal to the intersection of the transfer track 84 and the second track 82. In some embodiments, the length of the transfer track 84 can be generally about the same size as a cross-sectional width (e.g., a diameter) of the sleeve 12 and can be substantially smaller than the length of the sleeve 12. In the illustrated embodiment, the transfer track 84 does not constitute a portion of, or a continuation of, either of the first or second tracks 80, 82; rather, the transfer track 84 extends away from both other tracks 80, 82 at a point on each track 80, 82 that is spaced between the beginning and end of the tracks 80, 82 (e.g., at an intermediate or middle region of the tracks 80, 82).

In some embodiments the first track 80 includes an insertion portion 86 distal to the transfer track 84. The insertion portion 86 can be configured to be inclined in the proximal direction and terminate in a generally flat face 88 at the intersection between the first track 80 and the transfer track 84. In certain embodiments, the insertion portion 86 facilitates assembly of the cover 10. For example, during assembly of one arrangement the sleeve 12 is inserted through the proximal end 34 of the housing 14 and moved distally. The distal end 62 of the sleeve 12 is positioned so that the guide member 44 is generally aligned with insertion portion 86 of the first track 80. As the sleeve is moved distally the guide member 44 moves or rides up the incline of the insertion portion 86 until reaching the generally flat face 88, at which point the guide member 44 can snap to the bottom of the first track 80. Thereafter, the flat face 88 can inhibit or prevent disassembly of the cover 10 by presenting a barrier to the guide member 44 moving distally along the insertion portion 86. Further, the flat face 88 can direct the guide member 44 from the first track 80 to the transfer track 84 during retraction of the sleeve 12.

The cover 10 can have many different sizes, to accommodate the various sizes of needle and types of insertion and/or withdrawal procedures. For example, the cover 10 can be configured to accommodate needles used in medical (including dentistry) and veterinary procedures. In some embodiments the cover 10 can have an overall length of at least about 10 mm and/or less than or equal to about 100 mm, a housing 14 diameter of at least about 6 mm and/or less than or equal to about 20 mm, and a sleeve 12 diameter of at least about 3 mm and/or less than or equal to about 18 mm. In some embodiments, the sleeve 12 is longer than the housing 14; in some embodiments, the housing 14 is longer than the sleeve 12. Some examples of the cover 10 include a housing 14 with a length of about at least about 5 mm and/or equal to or less than about 50 mm and a sleeve with a length of about at least about 5 mm and/or equal to or less than about 50 mm. Other arrangements have a housing 14 with a length of at least about 15 mm and/or equal to or less than about 30 mm and a sleeve with a length of about at least about 10 mm and/or less than or equal to about 40-mm. Some embodiments of the cover are configured for use with needles 16 having a gauge of at least about 7 and/or less than or equal to about 34.

Figure 5:
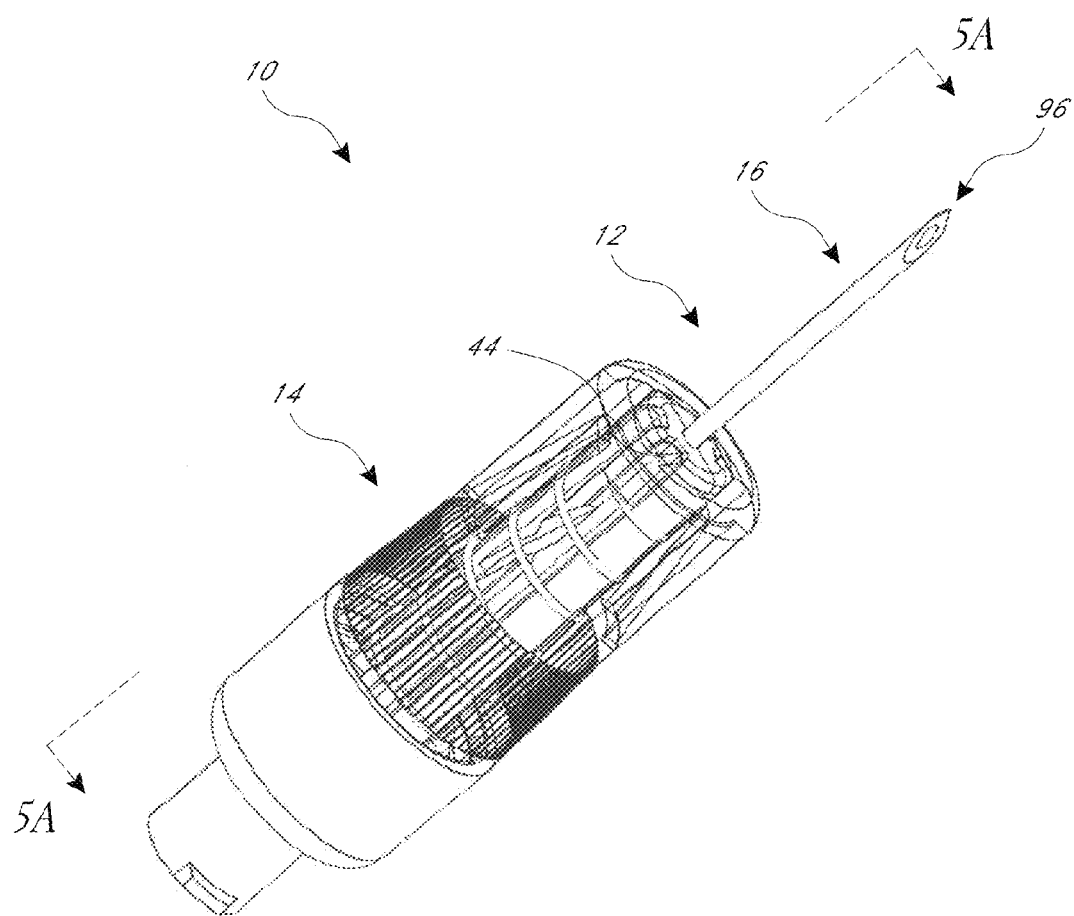
FIG. 5 illustrates a perspective view of the embodiment of FIG. 1 in a, fully retracted, fifth position.
Figure 5A:
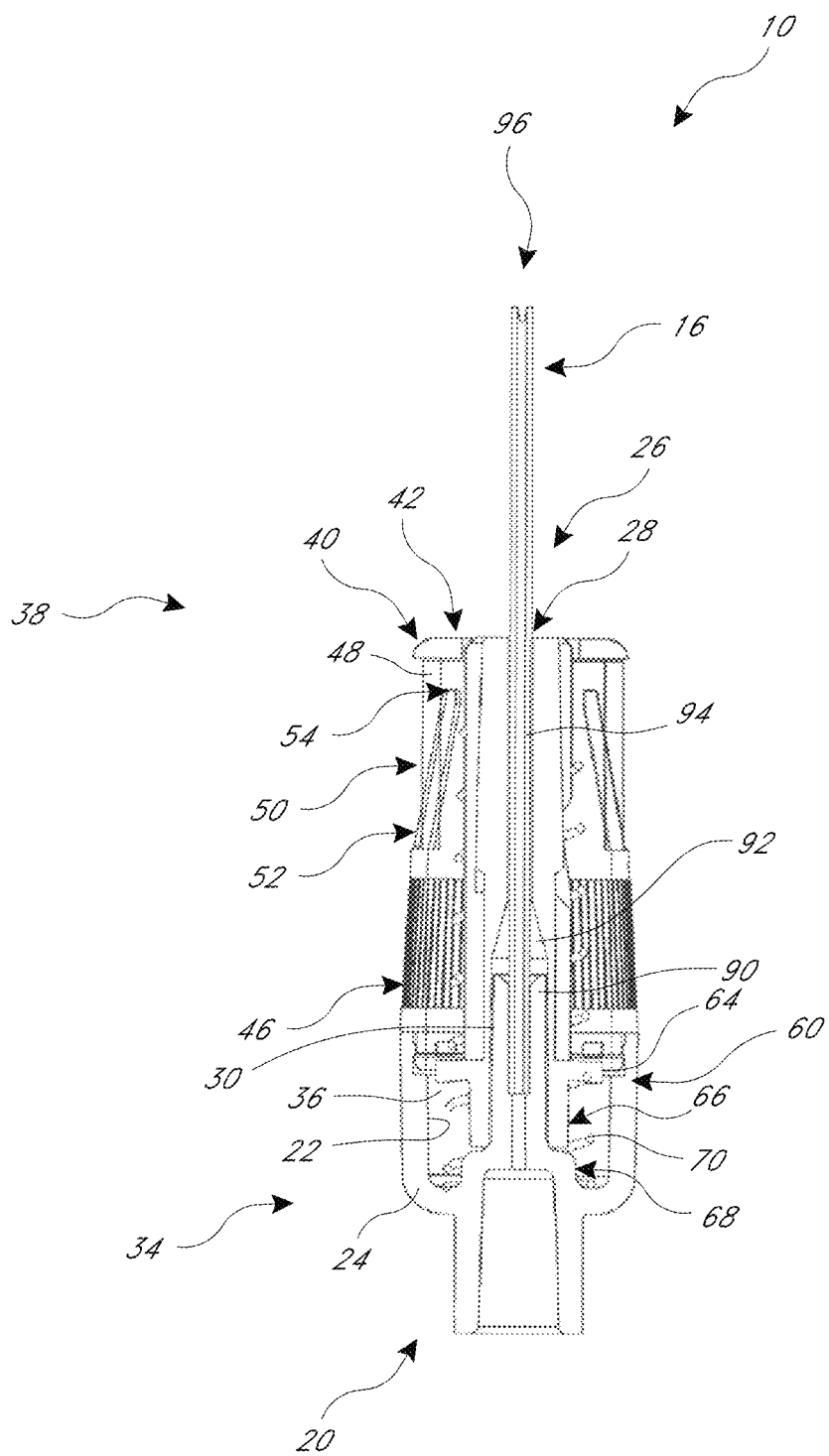
FIG. 5A illustrates a cross-sectional view along the line 5A-5A.

Many embodiments of the sleeve 12 and housing 14 are configured to provide a variety of potential insertion depths (the maximum penetration distance by the needle 16). This can assist in addressing, for example, dissimilar desired insertion depths between various procedures, e.g. intramuscular versus subcutaneous injections. In some embodiments, the potential insertion depth is determined by the distance the sleeve 12 travels from the fully extended position (FIG. 1) to the fully retracted position (FIG. 5). In some embodiments, the potential insertion depth is at least 1 mm and/or less than or equal to about 30 mm. In another construction, the potential insertion depth is at least 3 mm and/or less than or equal to about 70 mm. In some embodiments, there is a mechanism for determining, setting, and/or varying the potential insertion depth. For example, some embodiments include a stop member (not shown) extending radially inwardly from the inner surface 22 of the housing 14 and coupled to an axially movable ratchet, such that the proximal end 60 of the sleeve 12 abuts against the stop member when a desired level of insertion depth is attained. In some embodiments, the cover 10 includes indicia, e.g. a scale printed on the sleeve 12, to indicate the insertion depth of the needle 16.

The cover 10, and components thereof, can be formed using many manufacturing processes sufficient to provide the desired shape of the components. In some embodiments one or more components are made by a molding process, such as but not limited to injection molding, compression molding, blow molding, transfer molding, or similar. In some embodiments, one or more components are formed by forging, machining, casting, stamping, extrusion, a combination thereof, or the like.

In many embodiments, the cover 10 is constructed from a biocompatible material. In some arrangements one or more of the components of the cover 10 are plastic (e.g. polyetheretherketone) or metal (e.g., aluminum, titanium, stainless steel, or the like). In some embodiments, the housing 14 and/or the sleeve 12 are constructed of materials that are translucent, opaque, or otherwise optically distortive, such that some portion (such as the tip) or all of the needle 16 is not generally visible to the patient in a typical injection and/or aspiration procedure before, during, and/or after the injection and/or aspiration itself. Furthermore, aside from the channel 26 and the openings 48 in the housing 14 for the axial locking member 50, certain examples of the housing 14 and sleeve 12 are generally or entirely enclosed, e.g., devoid of slots, openings, or other apertures to inhibit a patient from viewing the needle 16. Thus, during an injection and/or aspiration procedure, any portion of the needle 16 that does not extend through the channel 26 can be obscured from view by the housing 14 and sleeve 12, and any portion of the needle 16 that extends through the channel 16 will be obscured from view because it is inside a vial or inside the patient. Of course, in some instances the entire needle 16 may not be fully obscured from view throughout the injection and/or aspiration procedure depending upon, among other things, the specific shapes of the distal end 62 of the sleeve 12, and the angle at which the needle 16 is inserted into the vial and/or the patient's skin or tissue. Because many people become anxious simply at the sight of a needle, the above-described features can significantly reduce the anxiety or fear of the patient and/or the person administering the injection and/or aspiration (who may also be the patient in cases of self-injection) to provide a more comfortable overall treatment experience.

In some embodiments, the distal end 62 of the sleeve 12 provides a pressure-receptor stimulation feature. Stimulation of the pressure-receptor nerves in the area of an injection and/or aspiration has been found to compete or interfere with stimulation of the pain receptor nerves. In many patients, stimulation of the pressure-receptor nerves in this manner reduces the perception of pain during insertion of the needle 16. Accordingly, in some constructions the distal end 62 includes a plurality of axially and/or radially extending ribs or projections 130 extending from the distal end 62 and away from the channel 26. For example, in some embodiments the ribs or projections are arranged generally in the shape of an asterisk centered about the aperture 28. During use, the projections 130 can be configured to engage the skin or tissue of a patient just prior to the tip 46 of the needle 16 coming into contact with the skin or tissue of the patient. In this way, the projections 130 apply pressure to the skin or tissue that stimulates the patient's pressure-receptor nerves prior to or at about the same time as insertion of the needle 16. In some embodiments, the distal end 62 comprises one or a series of depressions or protrusions, such as bumps, cones, rings, or the like, for engaging the skin or tissue of the patient and stimulating the patient's pressure-receptors prior to insertion of the needle 16. Some arrangements, the distal end 62 of the sleeve 12 is substantially flat, beveled, or the like. The specific configuration of the distal end 62 generally will vary depending upon, among other things, the intended field of use for the cover 10.

Some arrangements of the cover 10 include a therapeutic substance positioned at the distal end 62. For instance, in some embodiments the distal end 62 includes a topical anesthetic. In some embodiments, the distal end 62 includes an antiseptic, such as iodine or rubbing alcohol, and/or an antibiotic or antiviral medication. In some embodiments the therapeutic substance is applied or protected by a cap until the cover 10 is to be used.

In certain embodiments, aside from the bias of the spring 70, the sleeve 12 retracts substantially without impediment. The cover 10 need not require a first hand to provide pressure and/or operate the plunger on the syringe and a second hand to operate another feature (e.g., a clasp). In some embodiments, movement of the sleeve 12 automatically engages one or more of the locking members 50, 110. In some embodiments, movement of the sleeve 12 from an about fully retracted position to an about fully extended position automatically prevents or inhibits reuse of the cover 10. The cover 10 can be configured to facilitate one-handed retraction of the sleeve 12 (exposure needle 16), one-handed operation of the syringe, one-handed retraction of the sleeve 12 (covering of the needle 16), and/or one-handed engagement of features to inhibit reuse of the cover 10. Aside from retracting and/or extending the sleeve 12, the cover 10 can lock automatically and need not require external input (e.g. from manual manipulation of the user's fingers) to engage the axial locking member 50 and/or the rotational locking member 110.

In some embodiments, the cover 10 is manufactured by forming the housing 14 with the needle support portion 30, the distal opening 42, and the guide member 44. In embodiments in which housing 14 comprises multiple pieces, the manufacturing process can include the step of assembling the housing 14. A sleeve is formed that has the tracks 80-84. The guide member 44 is aligned with the insertion portion 86 of the first track 80. The sleeve 12 is slidingly moved through the distal opening 42. In some variants the guide member 44 moves up the incline in the insertion portion 86 and snaps into the first track 80 at about the flat face 88, thus preventing the guide member 44 from returning to the insertion portion 86. The needle 16 is coupled with the needle support portion 30 of the housing 14. The spring 16 is inserted into the central chamber 36 of the housing 14 and positioned to bias the sleeve 12.

Figure 1C:
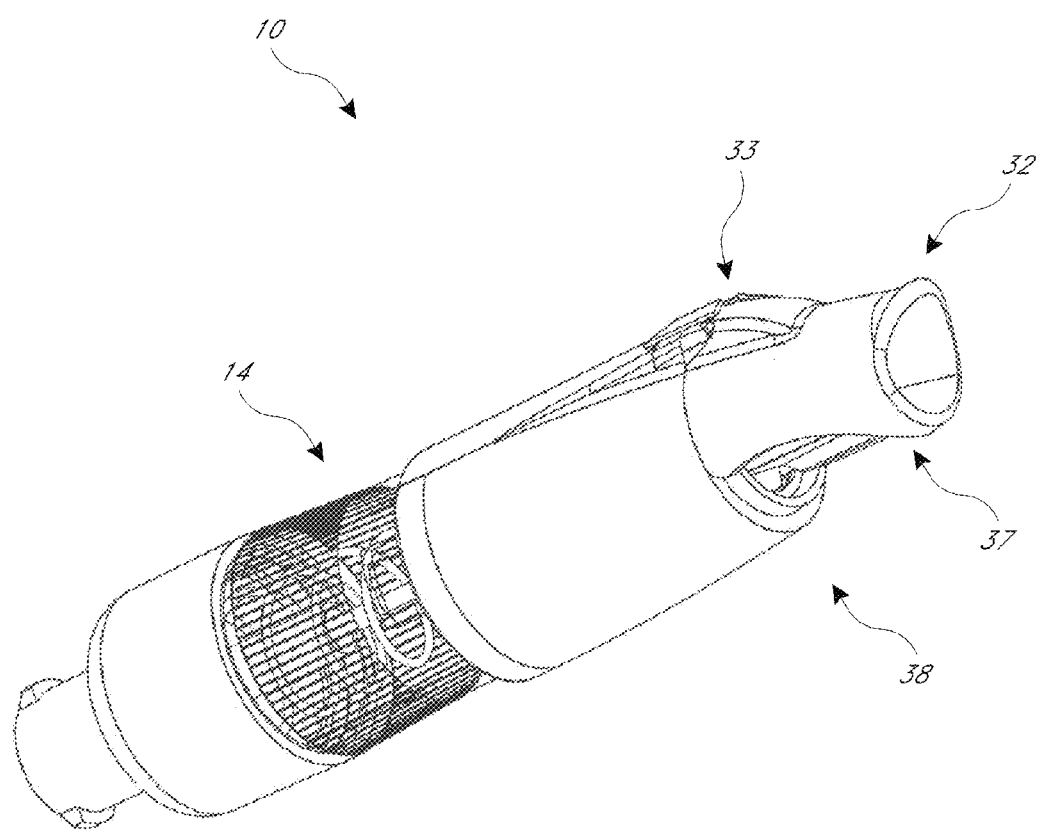
FIG. 1C illustrates a perspective view of the embodiment of FIG. 1 with a removable cap in the closed position.
Figure 1D:
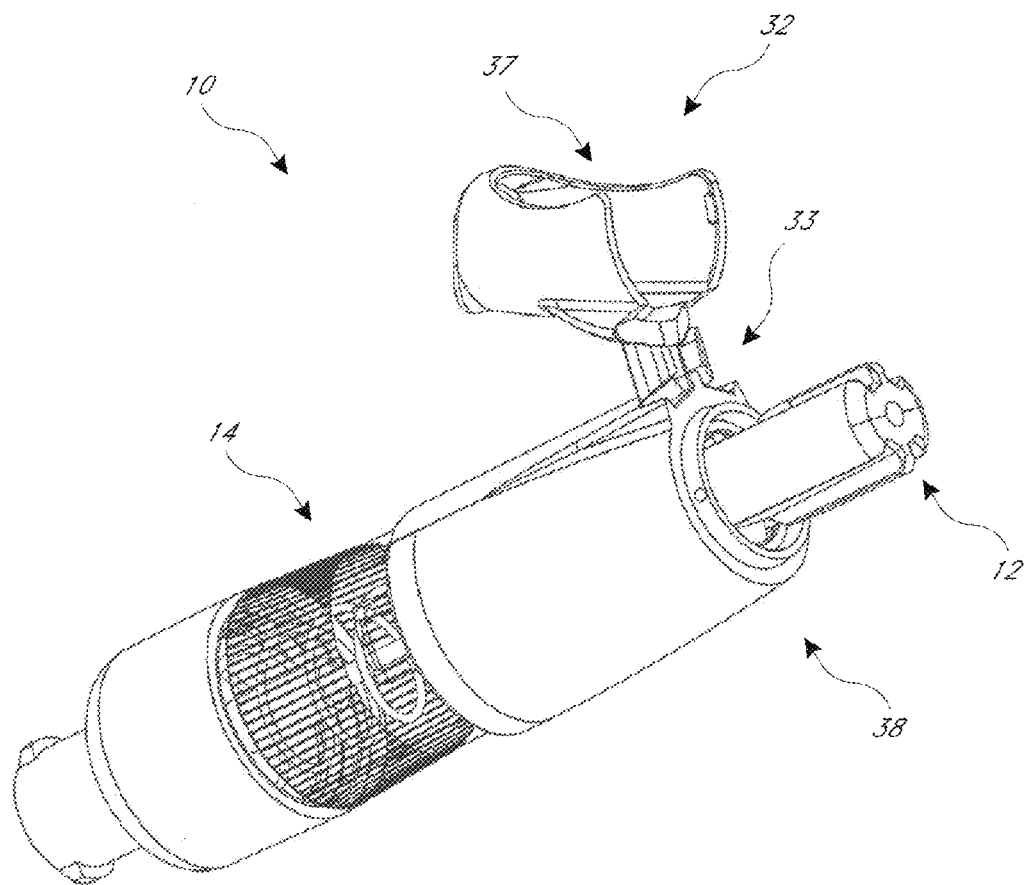
FIG. 1D illustrates a perspective view of the embodiment of FIG. 1 with a removable cap in the open position.

As shown in FIGS. 1C and 1D, the cover 10 can include a cap 32 that is removably coupled to the housing 14. A distal end of the cap 32 can move between an open position (FIG. 1C) and a closed position (FIG. 1D) by way of a hinge 33. In the closed position, the cap 32 reduces or prevents contamination of the sleeve 12 and distal end 38 of the housing 14, for example during shipping and storage of the cover 10. The cap 32 is generally kept in the closed position until just prior to an injection and/or aspiration procedure, at which time the cap 32 is moved to the open position and/or removed from the housing 14. In some embodiments, opening or removing the cap 32 before an injection and/or aspiration procedure does not expose the needle 16 because the sleeve 12 covers the needle 16, as shown in FIGS. 1 and 1A. Furthermore, if the cap 32 is removed, it may immediately be discarded because the sleeve 12 also covers the needle 16 once the injection and/or aspiration procedure is completed. The cap 32 can include an open portion 37 configured to, for example, facilitate opening and closing the cap 32.

In some embodiments, the cap can include a moveable or removable portion to assist in properly drawing a dose from a vial. For example, the cap 32 can be sized and configured to prevent the sleeve 12 from being retracted into the housing 14 a sufficient distance that the guide member 44 would enter the second track 82 or the transfer track 84. In some embodiments, the cap 32 is configured to prevent the sleeve 12 from retracting into the housing 14 far enough to engage the axial locking member 50 and/or rotational locking member 110, which may otherwise prevent further use of the device. In some embodiments, the cap 32 limits the retraction of the sleeve 12 such that the guide member 44 remains slidingly received in the first track 80.

To reduce anxiety, particularly in children, the cap 32, the housing 14, and/or the sleeve 12 may be provided with a variety of aesthetic designs such as rainbows, balloons, cartoon characters, or other illustrations that are generally considered pleasing and comforting to children. In this way, a child patient may be allowed to choose from a variety of different covers 10 prior to an injection and/or aspiration procedure. The cap 32, in addition or as an alternative to being colored or bearing indicia, may be fabricated to resemble a variety of different cartoon characters or other objects such that, upon removal from the housing 14 prior to an injection and/or aspiration procedure, the cap 32 may be presented to a child patient as a distraction during the injection and/or aspiration procedure. When fabricated to resemble a cartoon character or other object, the size and generally cylindrical shape of the cap 32 make it particularly well suited for use by the child as a finger puppet. Each of these features provides the opportunity to reduce the anxiety or fear experienced by many children before, during, and after an injection and/or aspiration procedure.

Figure 6:
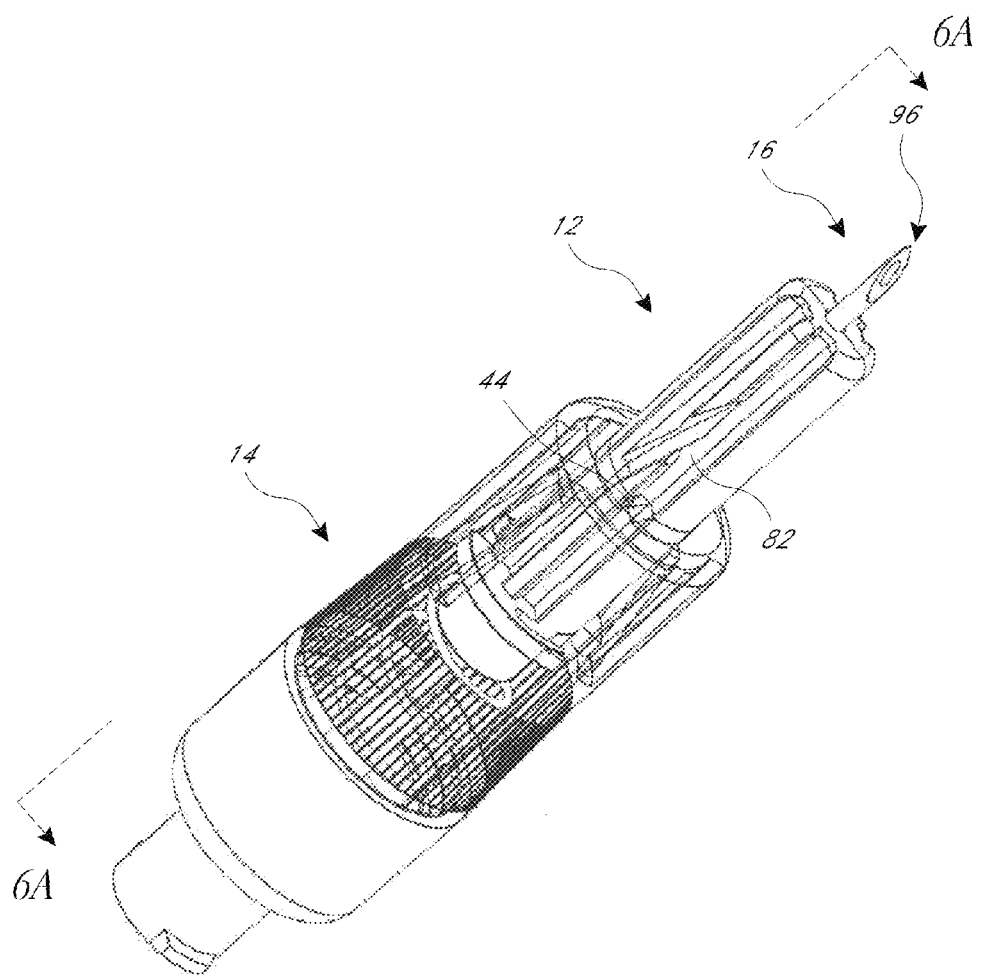
FIG. 6 illustrates a perspective view of the embodiment of FIG. 1 in a partially extended sixth position, in which the flange has engaged an axially locking member.
Figure 7:
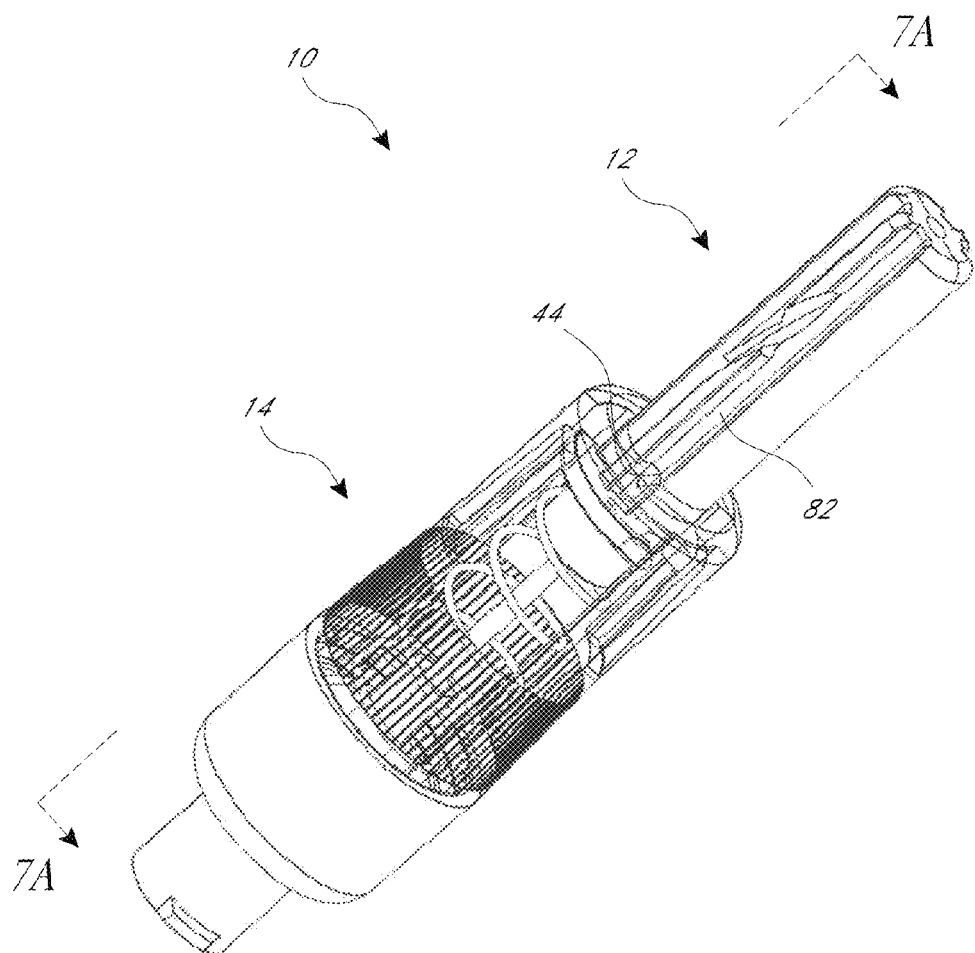
FIG. 7 illustrates a perspective view of the embodiment of FIG. 1 in a partially extended seventh position, in which the flange has further engaged the at least one axial locking member.
Figure 8:
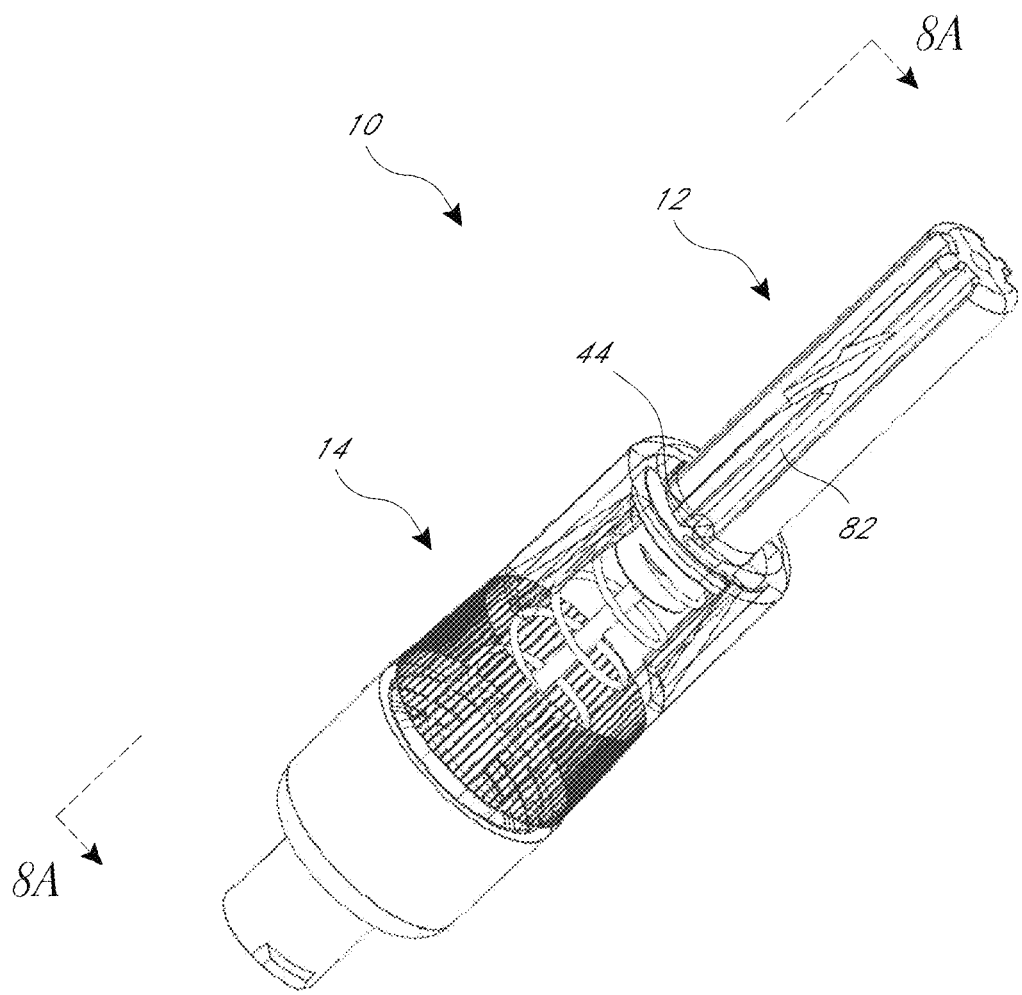
FIG. 8 illustrates a perspective view of the embodiment of FIG. 1 in a fully extended reuse-prevented, eighth position.
Figure 8A:
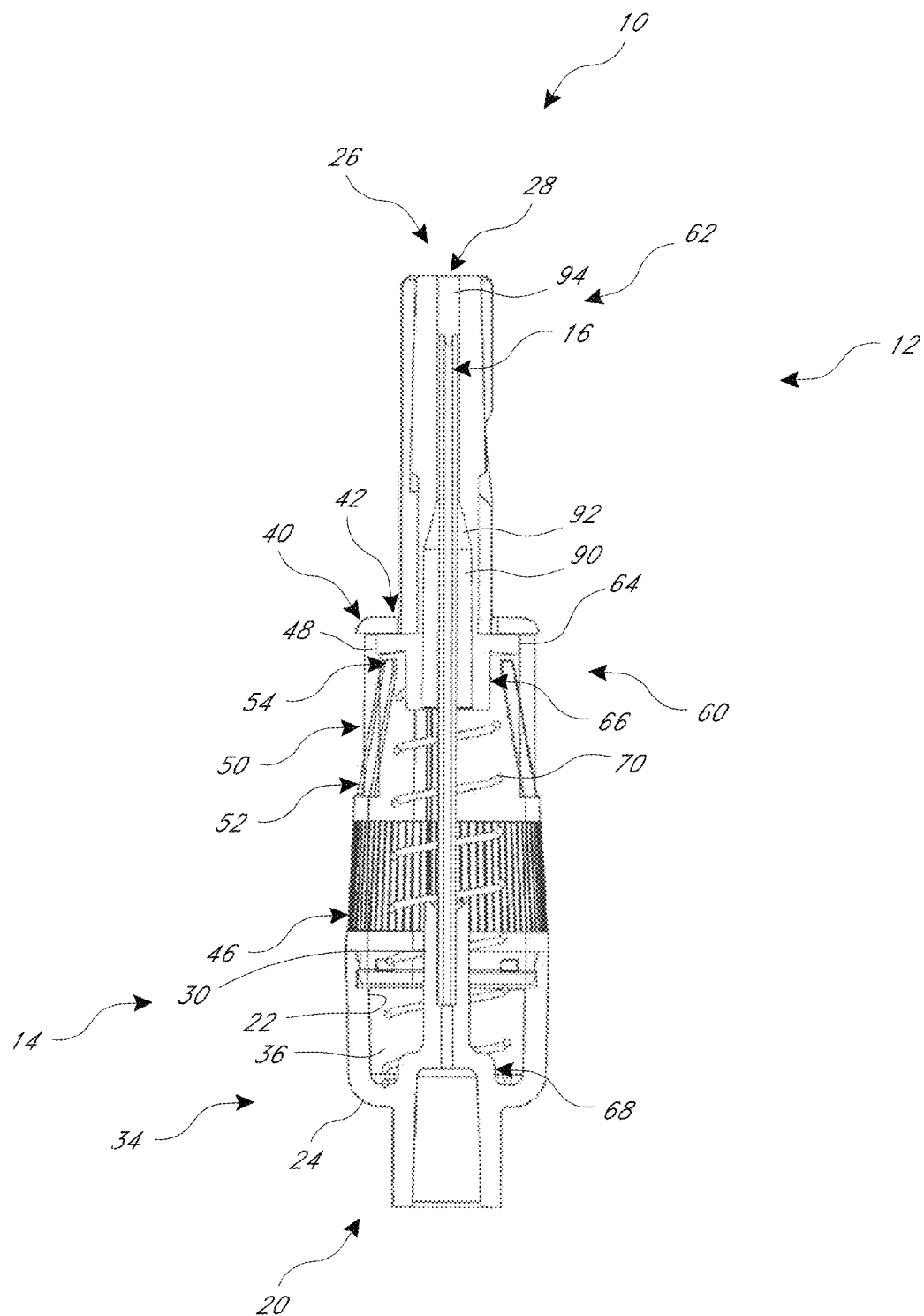
FIG. 8A illustrates a cross-sectional view along the line 8A-8A.

FIGS. 1-8A illustrate the cover 10 in various positions during an operating cycle that proceeds from the initial or ready-for-use extended configuration shown in FIG. 1, to an intermediate or a fully retracted position shown in FIG. 5, and to a final or reuse-prevention, extended configuration shown in FIG. 8A. It should be understood that the following presents an exemplary embodiment and is not intended to be limiting. It should be further understood that, although this embodiment describes the needle 16 being used to penetrate a patient's skin, the cover 10 is not limited to such use.

FIGS. 1-1C illustrate the cover 10 in the initial, ready-to-use configuration. As discussed above, the cover 10 is coupled to a syringe or other medical device, thus placing the syringe in fluid communication with the needle 16. After removing the cap 32 (if used) and taking surface prepatory steps (if appropriate, e.g. applying a disinfectant to the surface), the distal end 62 of the cover 10 can be placed against the patient's skin at the desired penetration site.

Figure 2:
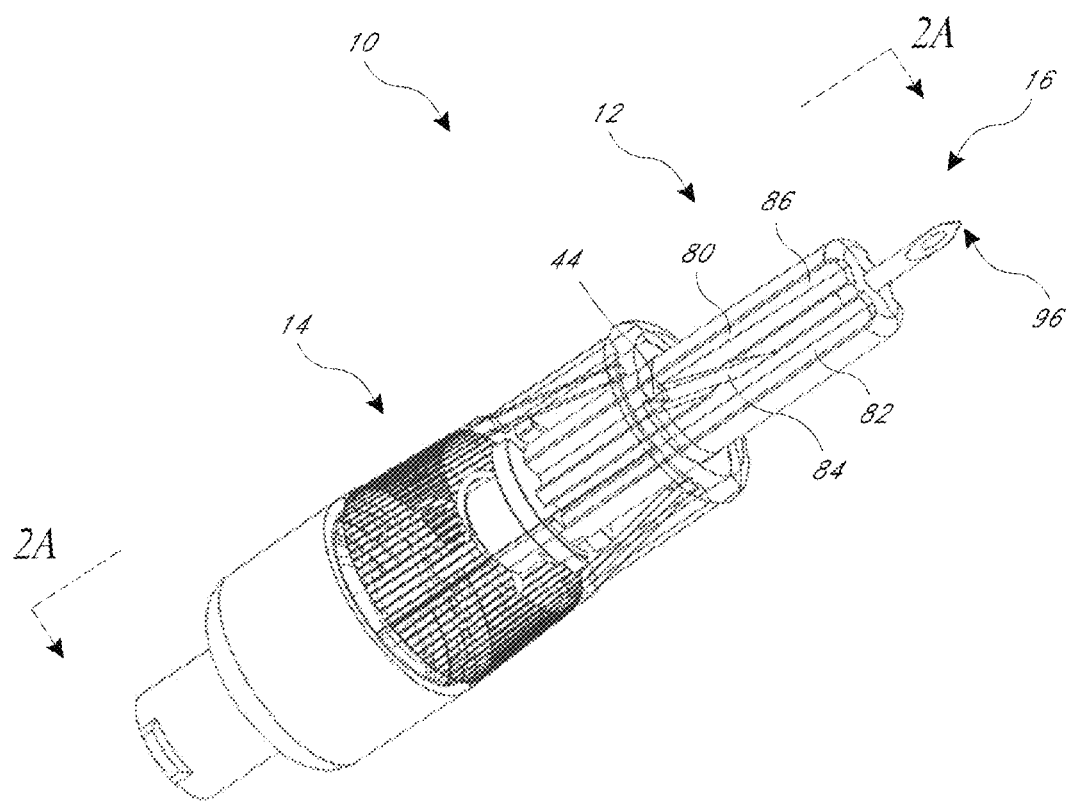
FIG. 2 illustrates a perspective view of the embodiment of FIG. 1 in a, partially retracted, second position.
Figure 2A:
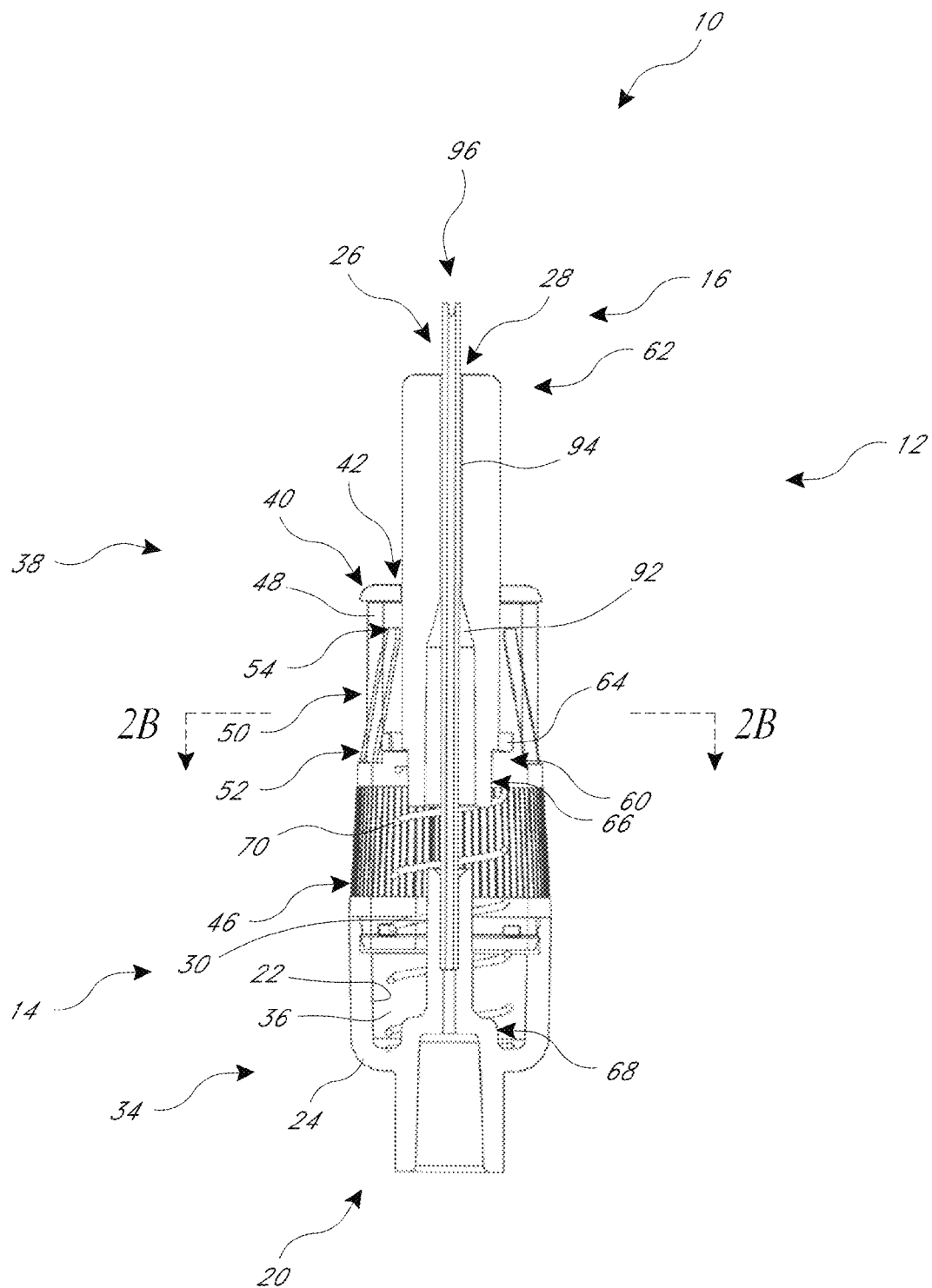
FIG. 2A illustrates a cross-sectional view along the line 2A-2A.
Figure 2B:
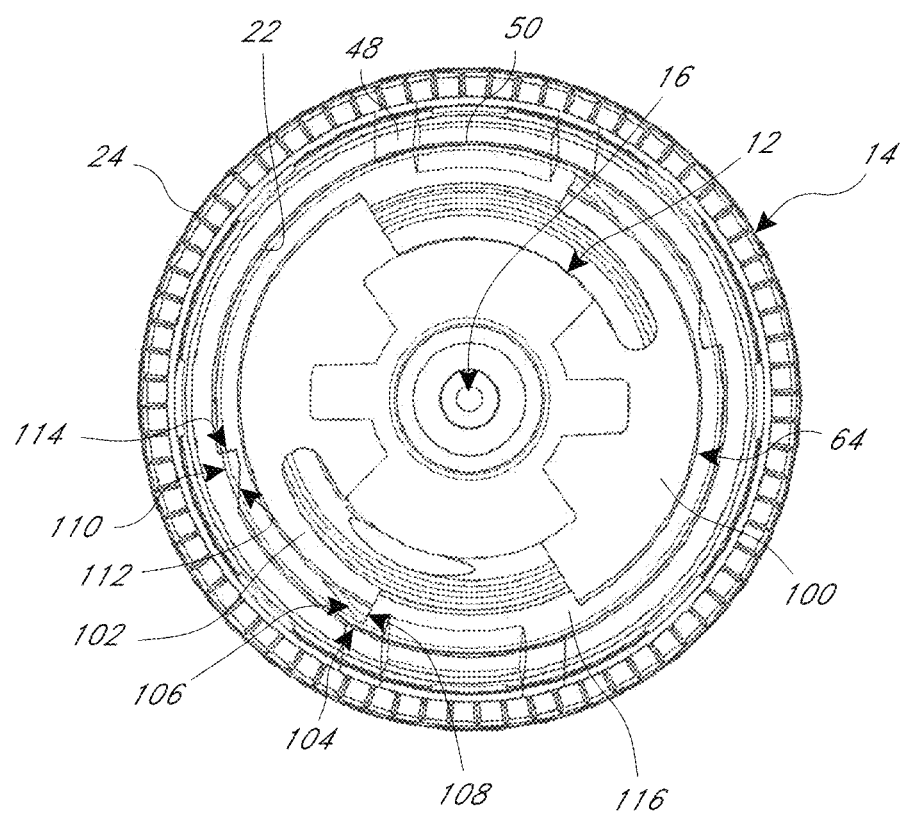
FIG. 2B illustrates a cross-sectional view along the line 2B-2B.

Referring now to FIG. 2, the cover 10 is illustrated in a first partially retracted configuration. Retraction of the sleeve 12 is generally initiated by a user applying pressure on the cover 10 and/or syringe in the distal direction, which thereby encourages the sleeve 12 proximally against the bias of the spring 70. This retraction of the sleeve 12 in turn exposes the distal tip 96 of the needle 16 and initiates penetration by the needle 16 into the patient's skin. The guide member 44 of the housing 14, which is positioned in the first track 80, directs the sleeve 12 to move axially until about the intersection of the first and transfer tracks 80, 84. Upon reaching the intersection of the first and transfer tracks 80, 84 the guide member 44 seats against the flat face 88, which directs the guide member into the transfer track 84. At this stage of the operation, the process may be reversed. If the distal pressure is removed, then the cover 10 can return to the original ready-for-use configuration shown in FIG. 1. As shown in FIGS. 2A and 2B, as the flange 64 of the sleeve 12 moves proximally, the axial locking member 50 passes through the notch 116 in the flange 64.

Figure 3:
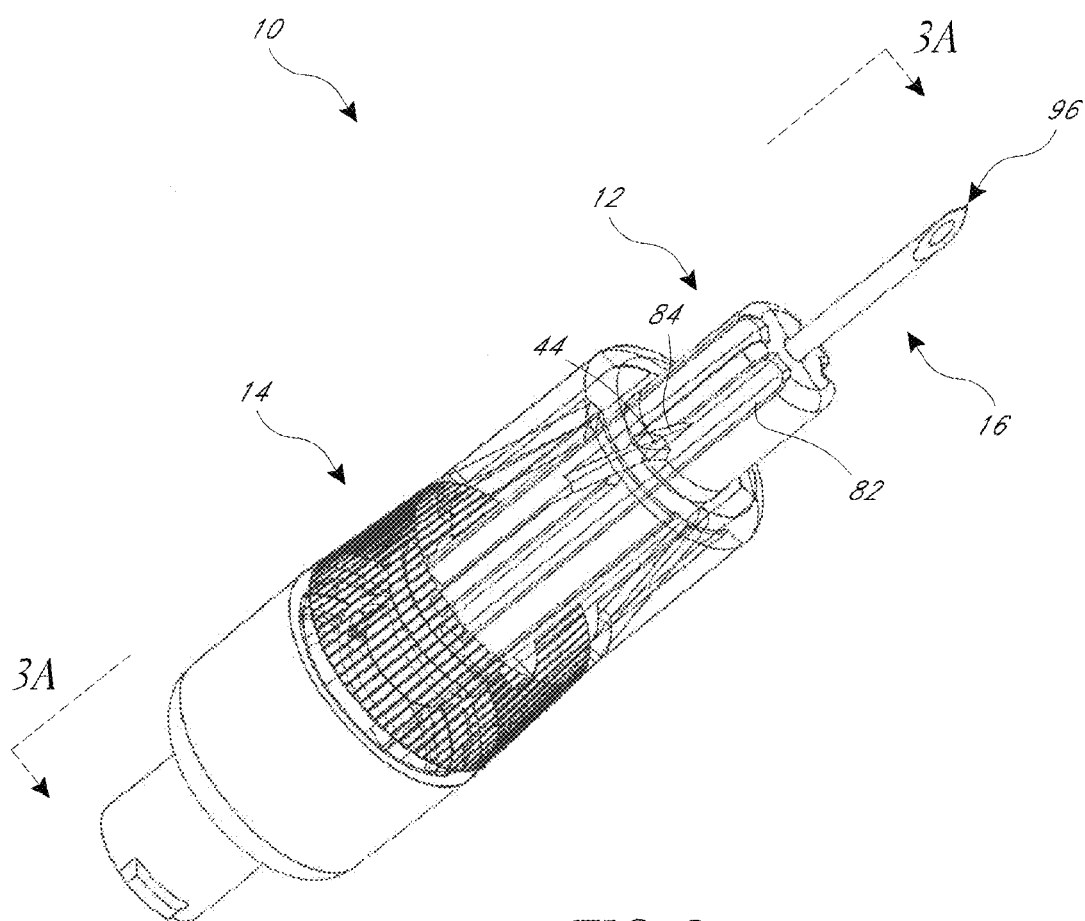
FIG. 3 illustrates a perspective view of the embodiment of FIG. 1 in a, partially retracted, third position, in which a flange has engaged a rotational locking member.
Figure 3A:
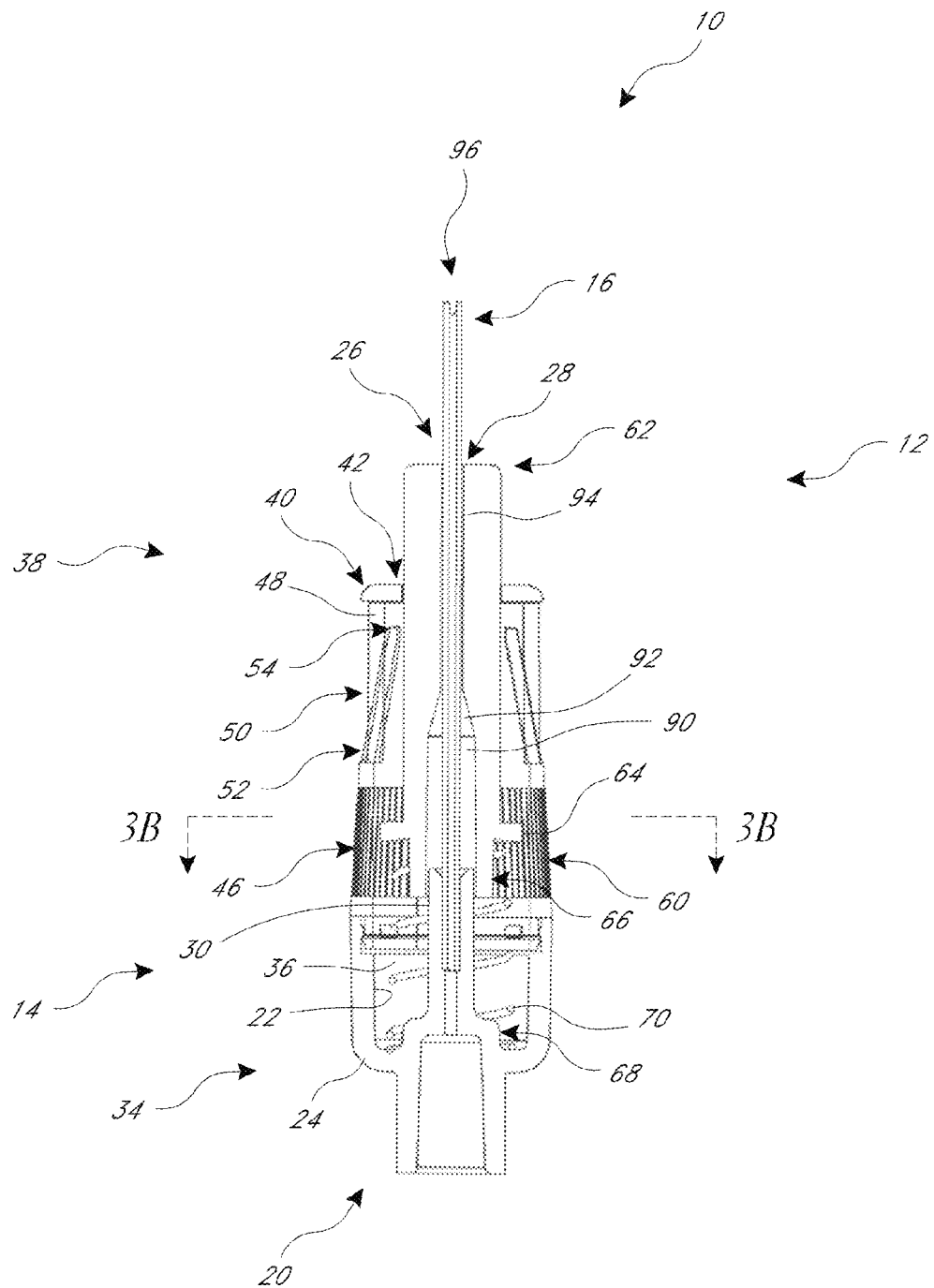
FIG. 3A illustrates a cross-sectional view along the line 3A-3A.
Figure 3B:
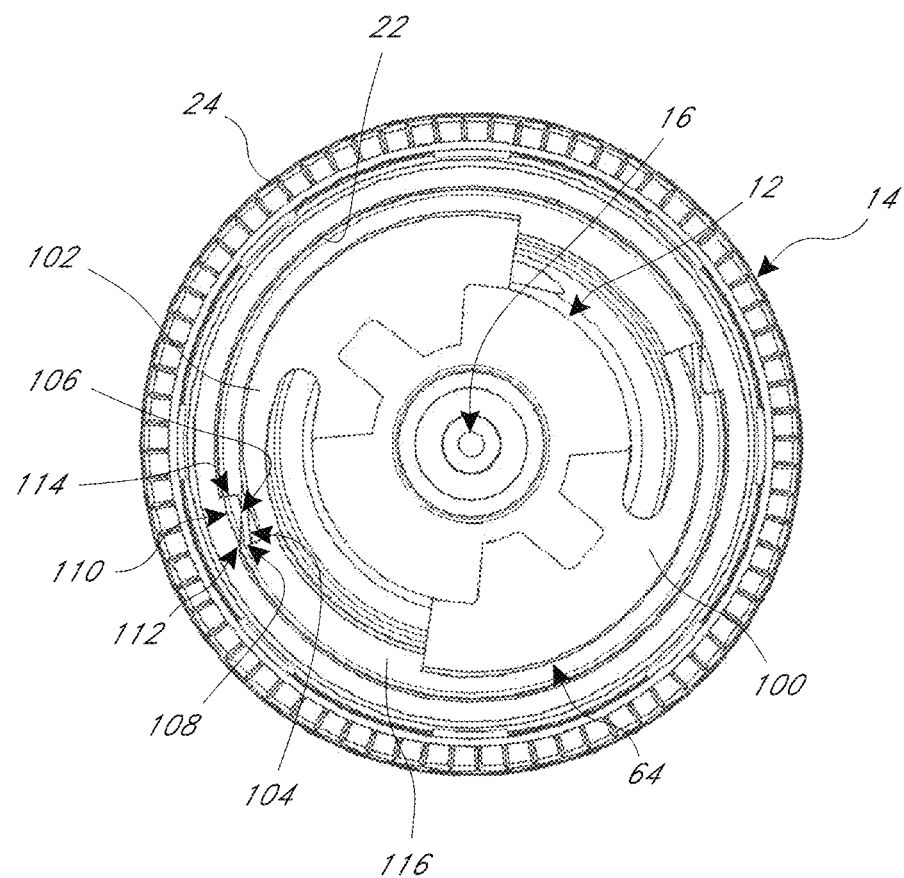
FIG. 3B illustrates a cross-sectional view along the line 3B-3B.

In the illustrated configuration of FIG. 3, the sleeve 12 has moved further proximally and the needle 16 has been further exposed. At this point, the sleeve 12 has moved sufficiently proximally that the proximal portion 90 of the channel 26 has started to receive the needle support portion 30, the axial locking member 50 has passed through the notches 116 in the flange 64 (FIG. 3A), and the guide member 44 is positioned in the transfer track 84. As the sleeve 12 moves proximally, the guide member 44 passes through the transfer track 84 thereby encouraging the sleeve 12 to rotate about the axis 18 approximately the number of degrees, e.g. at least about 5° and/or less than or equal to about 90°, that separate the first and second tracks 80, 82. Rotation of the sleeve 12 in turn rotates the flange 64, including the impeding member 102. As shown in FIG. 3B, the inclined face 106 of the impeding member 102 rotates toward the inclined face 112 of the rotational locking member 110. Continued rotation of the impeding member 102 of the flange 64 of the sleeve 12 slidably engages the inclined faces 106, 112, thereby deflecting the impeding member 102 radially inward and producing a slight but noticeable resistance. In some embodiments, as illustrated, the length of the impeding member 102 can be generally about the same size as or shorter than the length of the transfer track 84.

Figure 4:
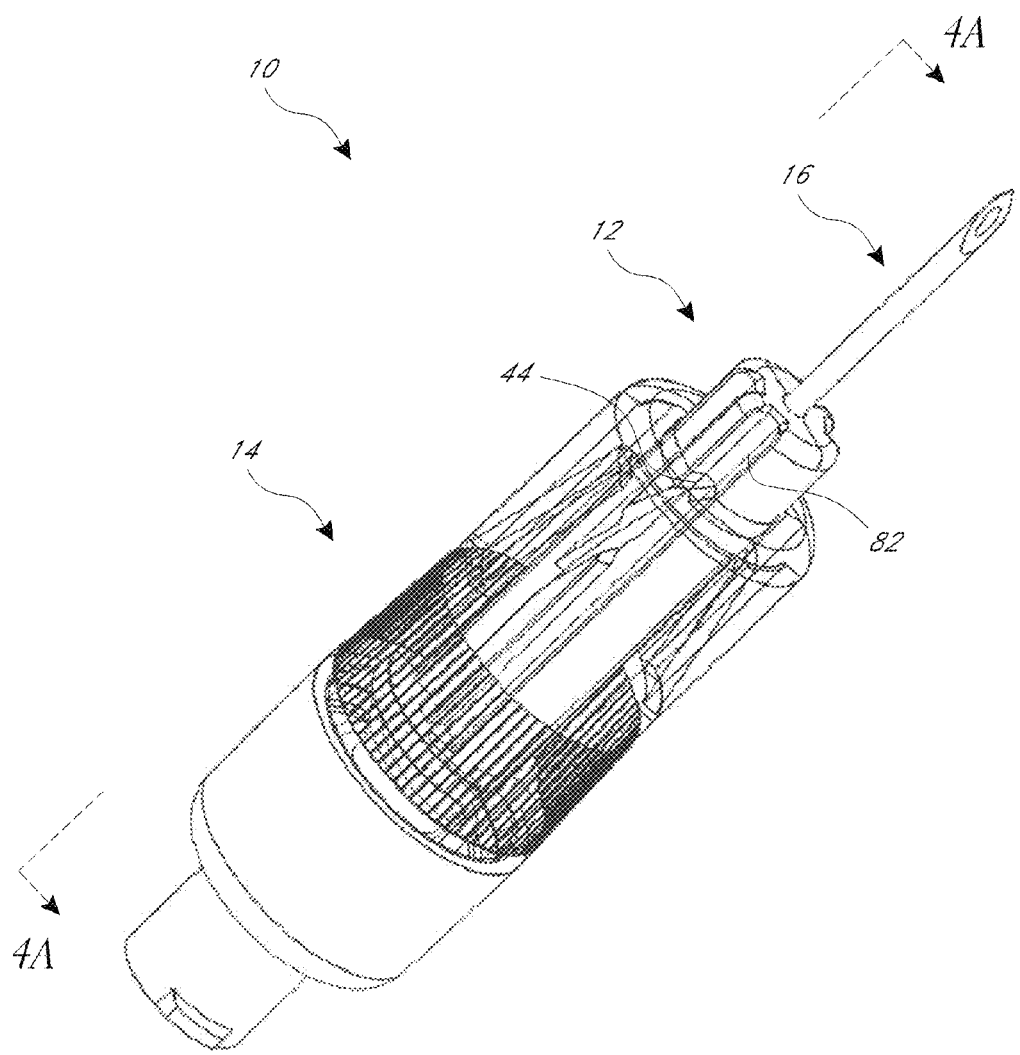
FIG. 4 illustrates a perspective view of the embodiment of FIG. 1 in a, partially retracted, fourth position, in which the rotational locking member has been locked.
Figure 4A:
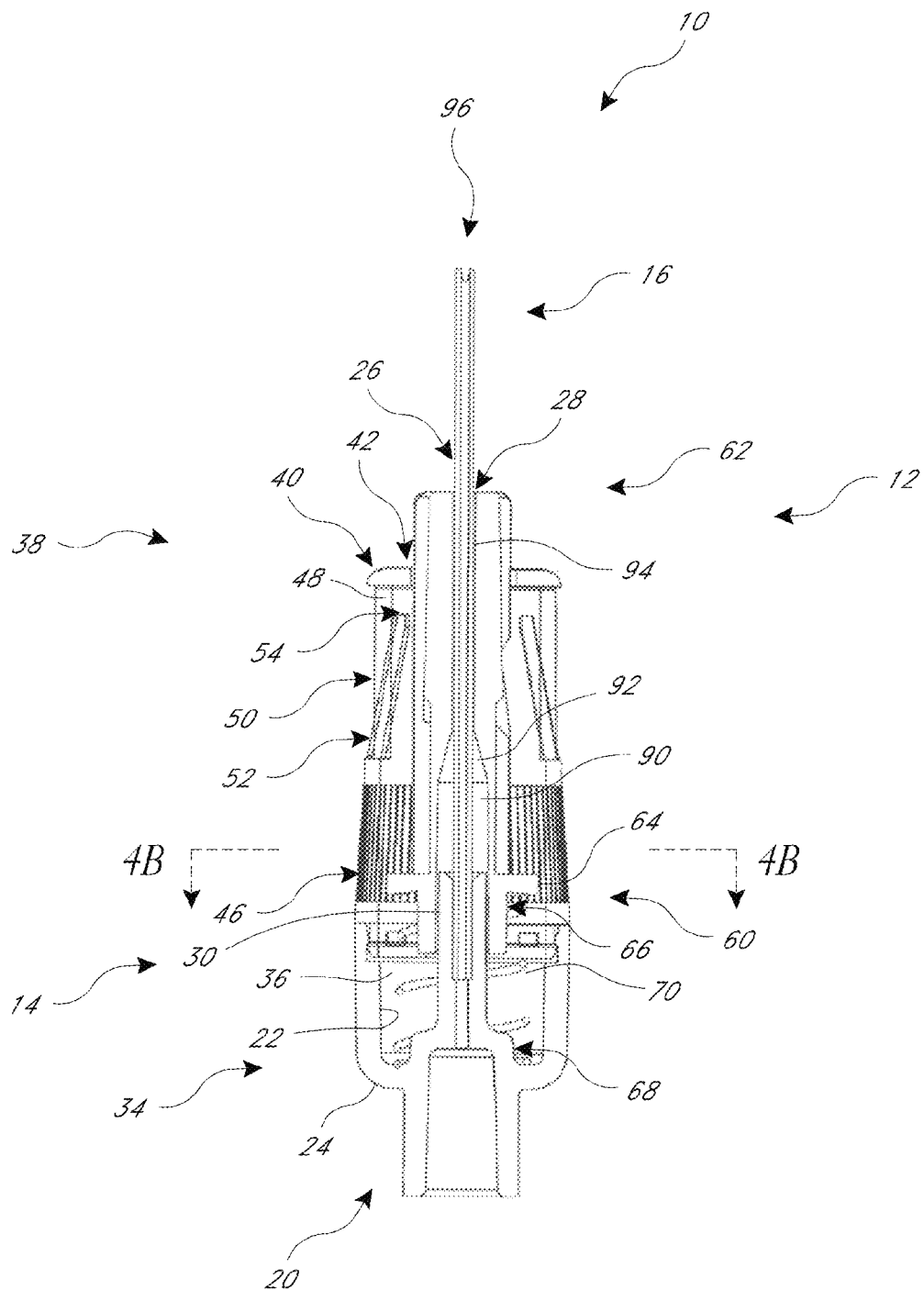
FIG. 4A illustrates a cross-sectional view along the line 4A-4A.

Turning to the illustrations of FIGS. 4 and 4A, the sleeve 12 has continued to retract into the housing 14, which has further exposed the needle 16. The guide member 44 has shifted from the transfer track 84 to the second track 82, thus further rotating the sleeve 12 with respect to the housing 14.

Figure 4B:
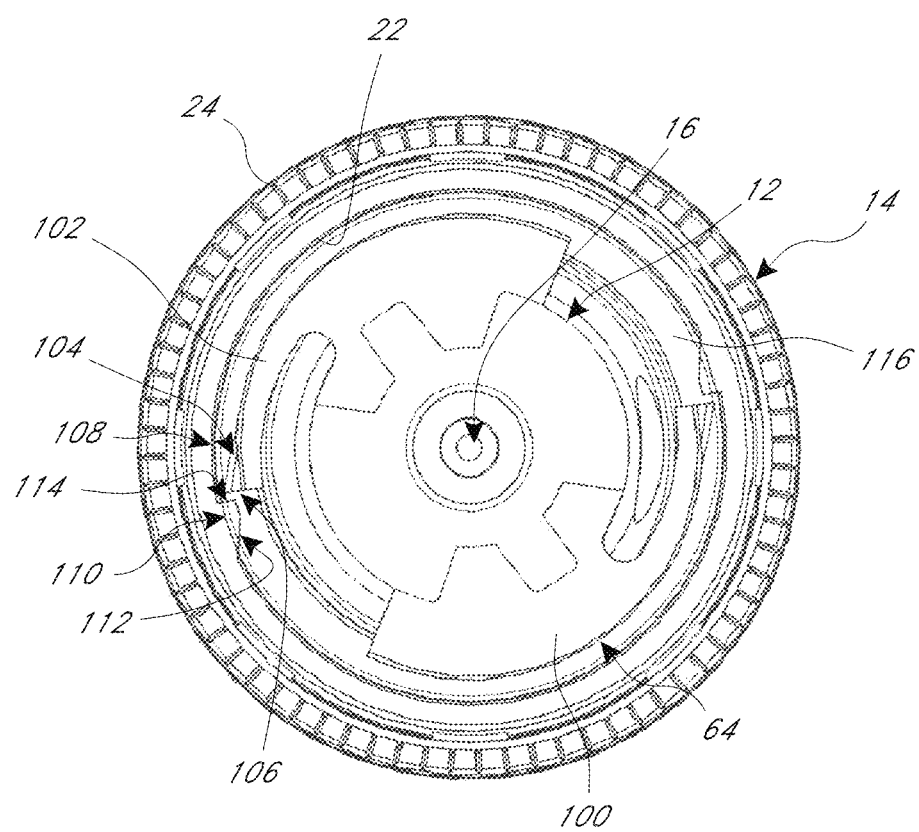
FIG. 4B illustrates a cross-sectional view along the line 4B-4B.

The needle support portion 30 has been further received by the proximal portion 90 of the channel 26. As shown in FIG. 4B, once the inclined face 106 of the impeding member 102 rotated beyond the zenith of the inclined face 112 of the rotational locking member 110, the impeding member 102 deflected radially outward, thus returning to about its radial position shown in FIG. 2B. In this configuration, the generally flat faces 108, 114 present a physical stop thereby inhibiting counter-rotation of the sleeve 12. This in turn prevents the guide member 44 from returning into the transfer track 84, as will be discussed below. In some embodiments, the outward deflection of the impeding member 102 produces a tactile vibration and/or an audible sound, e.g. "snap," which can provide verification that the rotational locking member 110 has been locked and counter-rotation is prevented.

The fully retracted configuration of the cover 10 is illustrated in FIG. 5. The needle 16 is at its apex of exposure, presenting the longest exposed needle length. The distal end 62 of sleeve 12 is generally flush with distal end 38 of housing 12. The proximal portion 90 of the channel 26 has approximately fully received the needle support portion 30. The spring 70 is compressed to generally its fully compressed configuration. In several embodiments, this is the configuration in which the syringe's contents are injected, via the hub 20 and needle 16, into the patient.

Figure 6A:
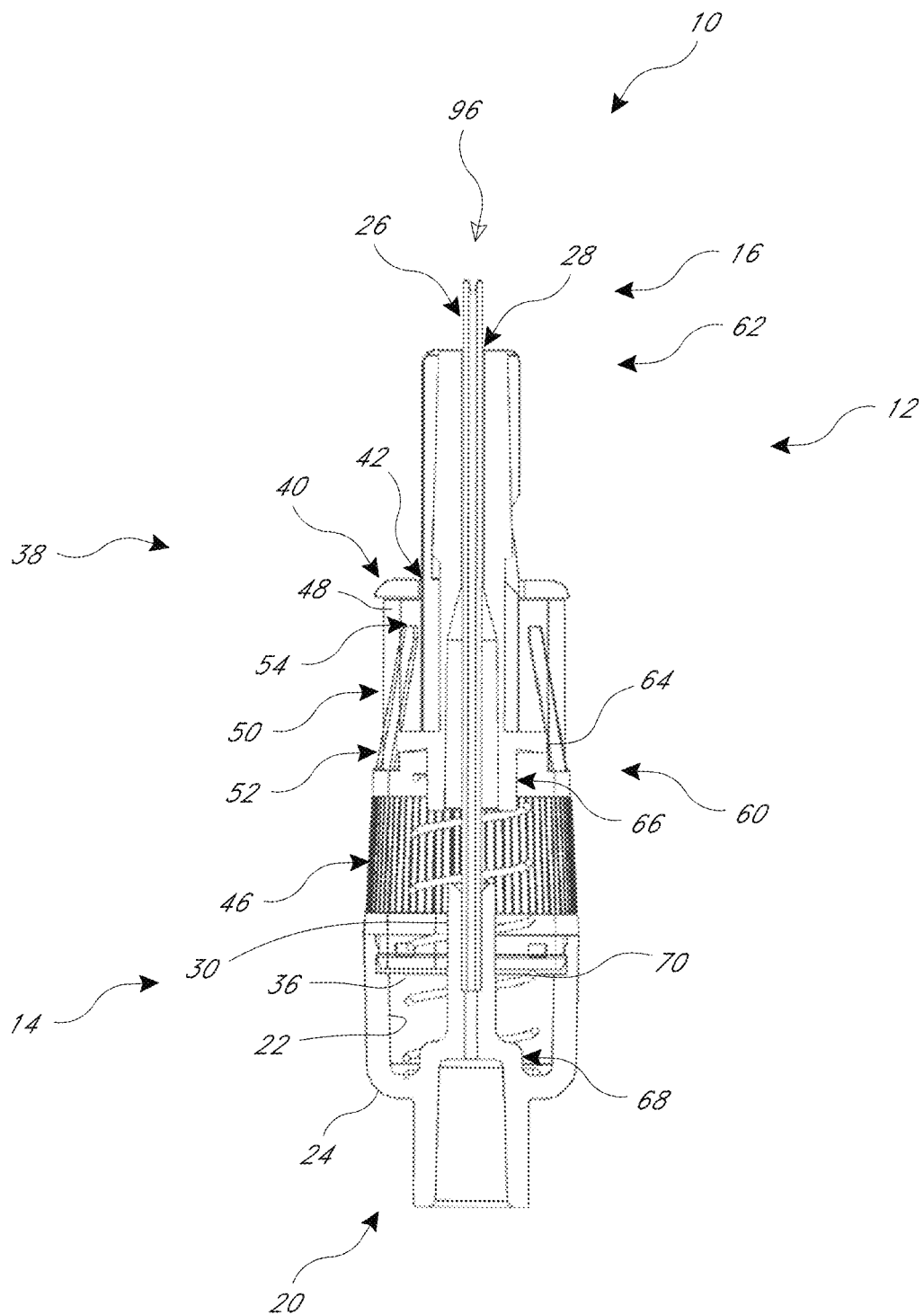
FIG. 6A illustrates a cross-sectional view along the line 6A-6A.

Turning to FIGS. 6 and 6A, an initial stage of withdrawal of the needle 16 is shown. Withdraw generally initiates when the user pulls away the syringe from the patient, or when the user applies less distal pressure on the cover 10 and/or syringe, thus permitting the bias of the spring 70 to distally extend the sleeve 12. As the sleeve 12 distally extends it receives the needle 16 into the channel 26 thereby covering at least a portion (such as the distal end) of the needle 16. The distal movement of the sleeve 12 also slides the guide member 44 along the second track 82. The engagement of the generally flat faces 108, 114 inhibits or prevents counter-rotation of the sleeve 12, which in turn prevents the guide member 44 from shifting into the transfer track 84 at intersection between the second track 82 and the transfer track 84.

Figure 7A:
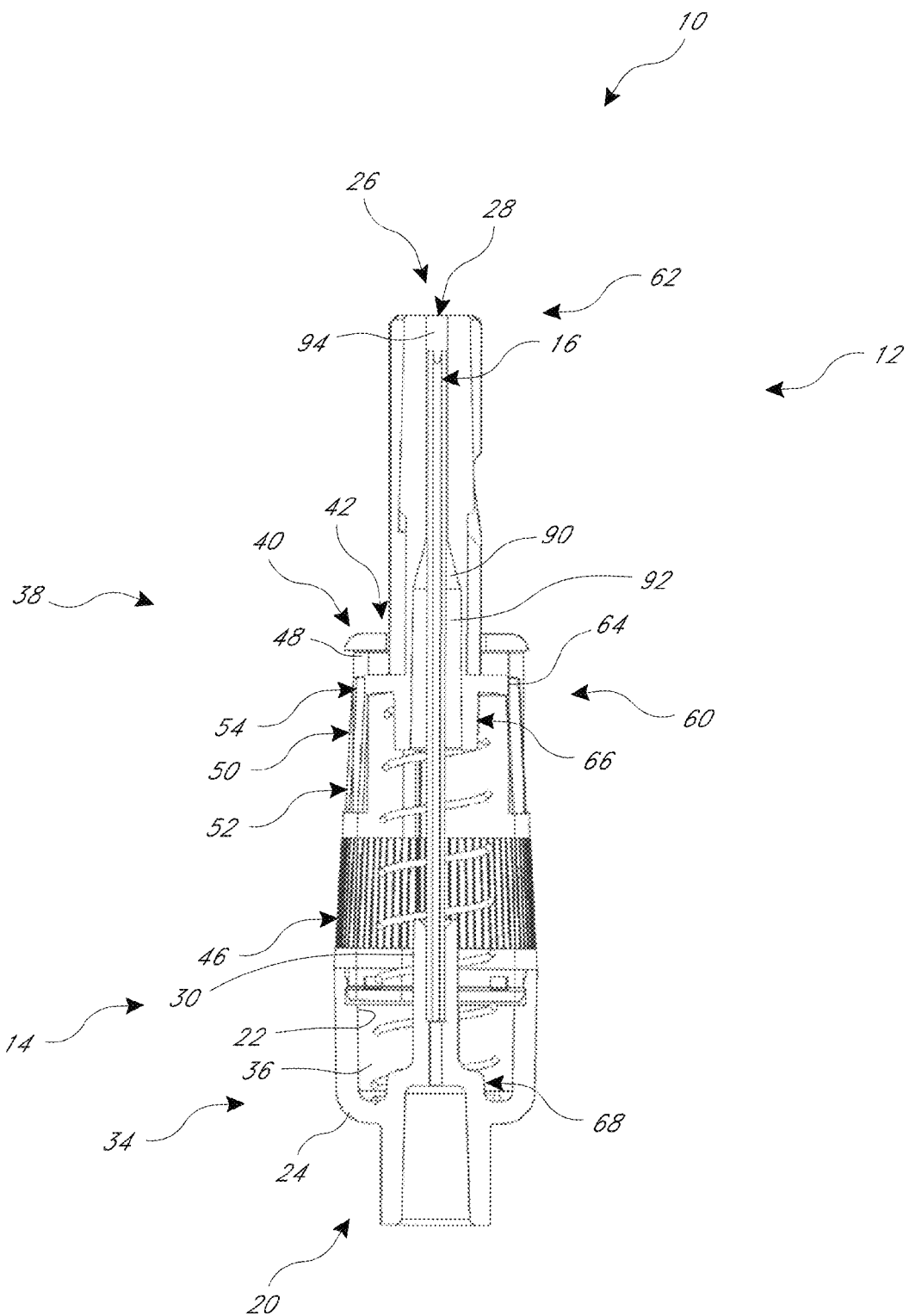
FIG. 7A illustrates a cross-sectional view along the line 7A-7A.

FIGS. 7 and 7A illustrate a configuration of the cover 10 in which the sleeve 12 has been further extended and the needle 16 has been further covered. At this stage in the operation, as the sleeve 12 moves distally, the outwardly extending portion 100 of the flange 64 slidingly engages the axial locking member 50. The outwardly extending portion 100 of flange 64 encourages the axial locking member 50 radially outward and produces a slight but noticeable resistance.

Moving now to FIGS. 8 and 8A, an extended, reuse-prevention, configuration of the cover 10 is depicted. The sleeve 12 has been fully extended and fully covers the needle 16. The spring 70 has moved the sleeve 12 distally until the flange 64 seated against the shoulder 40. Upon the outwardly extending portion 100 of the flange 64 moving distal of the second end 54 of the axial locking member 50, the axial locking member 50 snapped radially inward with respect to the outwardly extending portion 100 of the flange 64. The axial locking member 50 thus presents a physical stop to inhibit the sleeve 12 from being proximally retracted again. In some embodiments, the inward deflection of the least one axial locking member 50 produces a tactile vibration and/or an audible sound, e.g. "snap," which can provide verification that the axial locking member 50 has been engaged.

FIGS. 9-14A illustrate another embodiment of the cover 10. Several features and components of the cover 10a are similar in form and function to those described above with respect to the cover 10, and have been provided with like numerals. To the extent components of the cover 10a differ slightly from those of the cover 10 described above, some those differences are described and explained below. Any features and/or components of the disclosed embodiments can be combined or used interchangeably.

Figure 9:
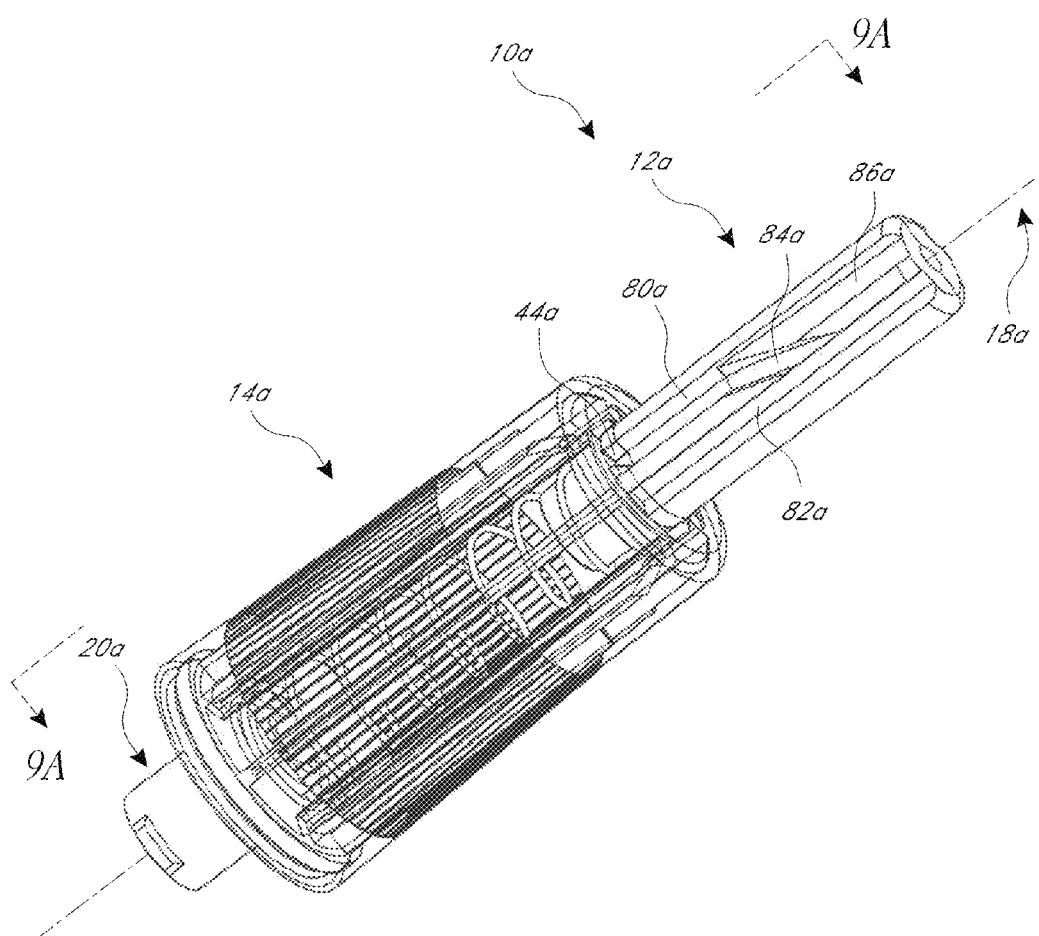
FIG. 9 illustrates a perspective view of another embodiment of a needle cover.
Figure 9A:
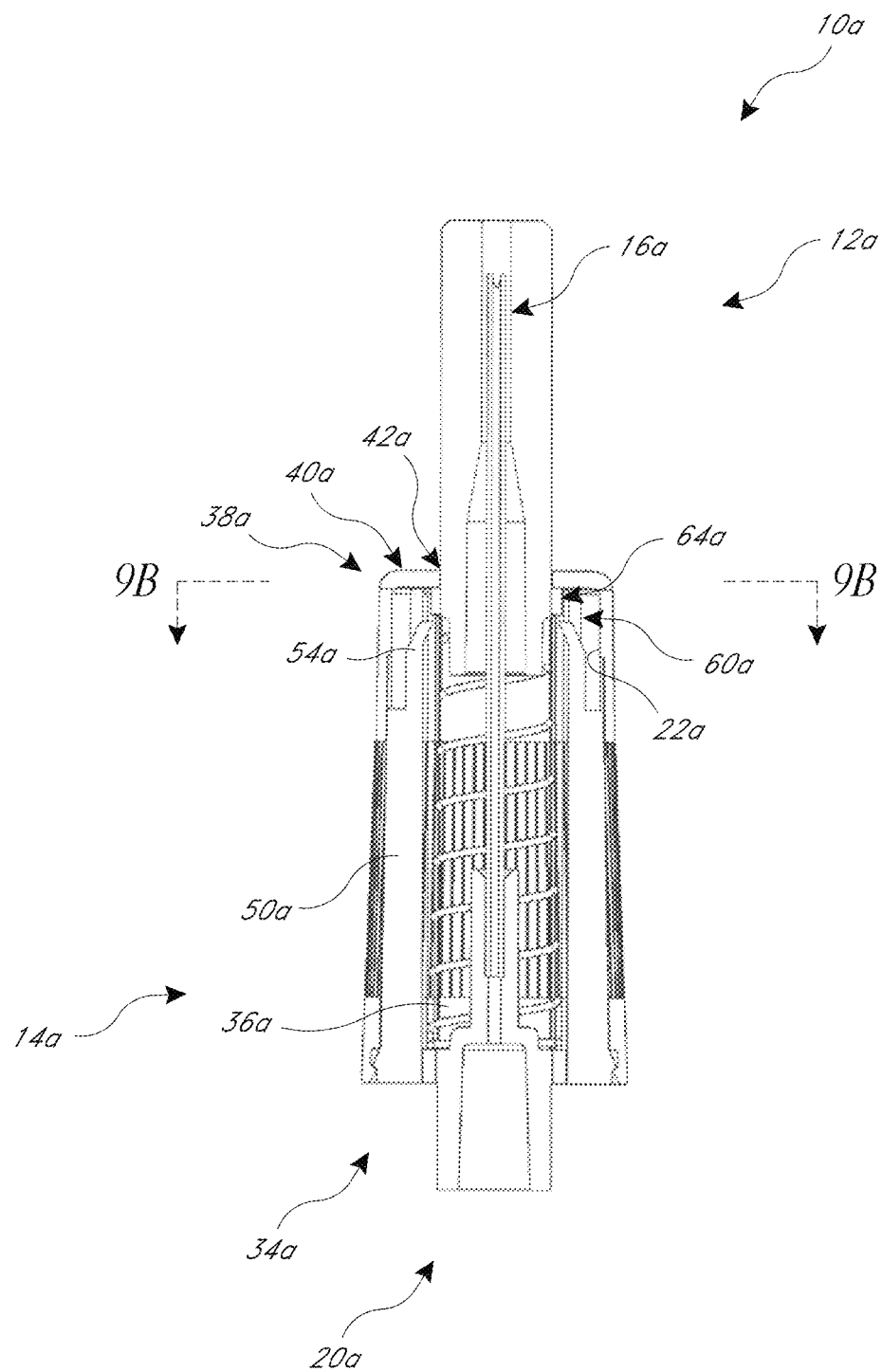
FIG. 9A illustrates a cross-sectional view along the line 9A-9A in a ready for use, fully extended and unlocked, position.
Figure 9B:
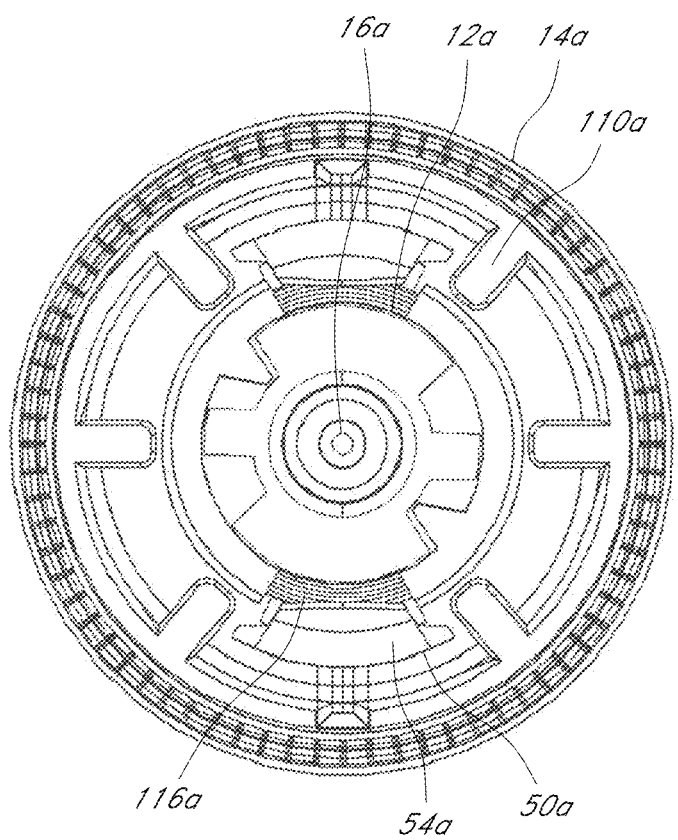
FIG. 9B illustrates a cross-sectional view along the line 9B-9B.

In the embodiment illustrated in FIGS. 9-9B, the cover 10a includes a generally cylindrical housing 14a that comprises an axis 18a, along which a needle 16a is positioned. A distal end of the housing 14a couples to a sleeve 12a configured to translate along and at least partially rotate about the axis 18a. A proximal end 60a of the sleeve 12a couples to a radially outwardly extending flange 64a. A proximal end 34a of the housing 14a comprises or is coupled to a hub 20a. An inside surface 22a of the housing 14a includes a central chamber 36a. One or more ribs 110a extend radially inwardly from the inner surface 22a. A distal end 38a of the housing 14a includes a radially inwardly extending shoulder 40a that includes an opening 42a that communicates with the chamber 36a. The opening 42a slidingly receives the sleeve 12a that in turn receives and covers the needle 16a. A guide member 44a extends radially inwardly from the shoulder 40a and is configured to engage one or more tracks formed in the sleeve 12a.

With continued reference the illustrations of FIGS. 9-9B, the housing 14a includes at least one axial locking member 50a. The axial locking member 50a can extend generally parallel to the axis 18a from the inner surface 22a of the proximal end 34a of the housing 14a to near the inner surface 22a of the distal end 38a of the housing 14a. A portion of the axial locking member 50a extends about parallel to the axis 18a and is configured to avoid interference with a flange 64a of the sleeve 12a as the sleeve 12a moves axially. A second end 54a of the axial locking member 50a angles radially inward. As shown in FIG. 9B, in some arrangements the second end 54a of the axial locking member 50a aligned with a notch 116a in a flange 64a, thereby permitting the second end 54a to pass though the notch 116a.

Figure 10:
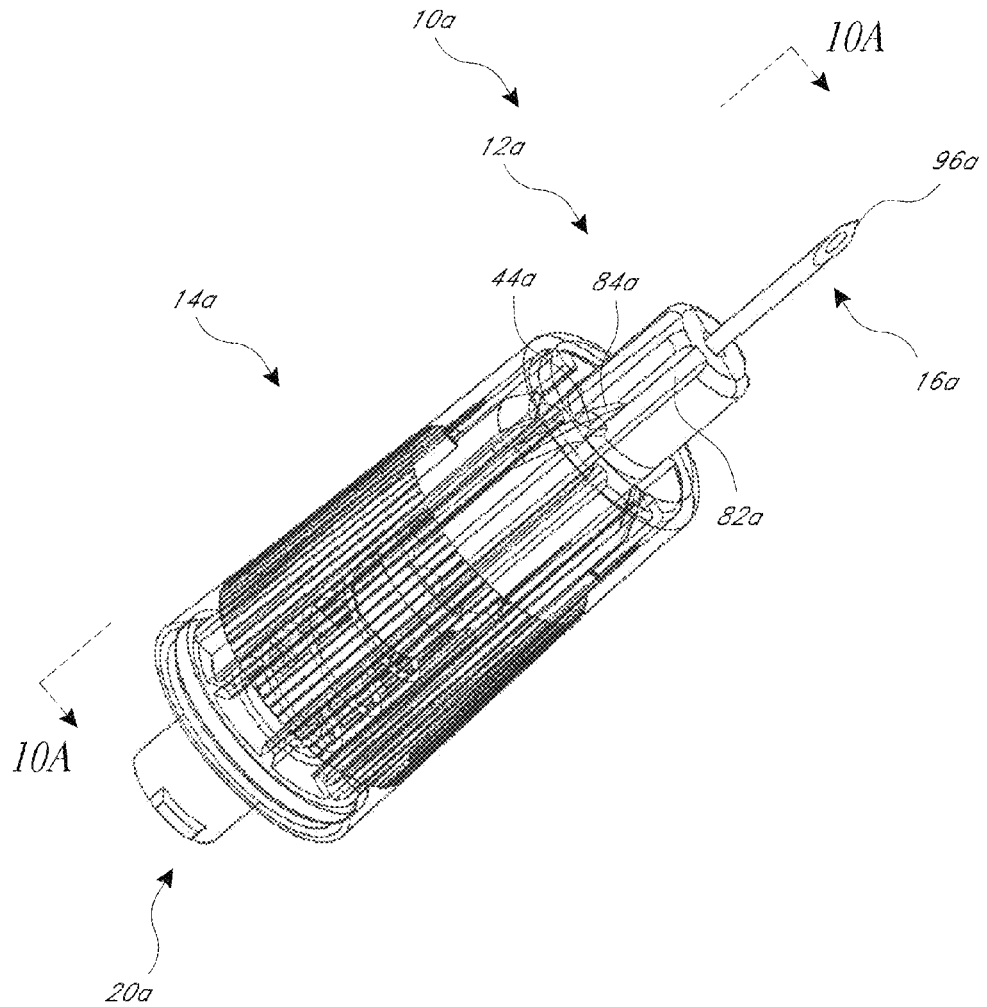
FIG. 10 illustrates a perspective view of the embodiment of FIG. 9 in a partially retracted position.
Figure 10A:
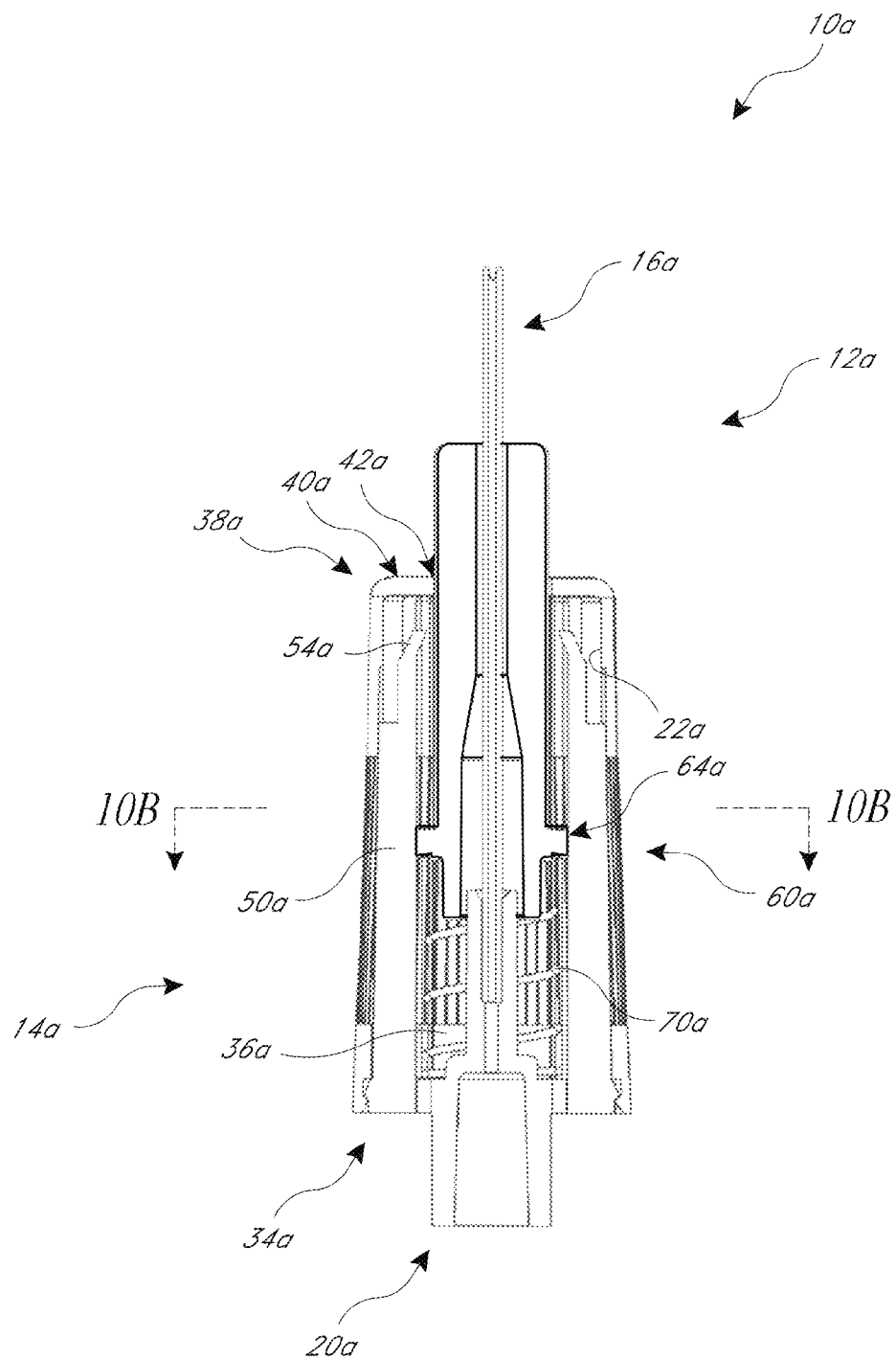
FIG. 10A illustrates a cross-sectional view along the line 10A-10A.
Figure 10B:
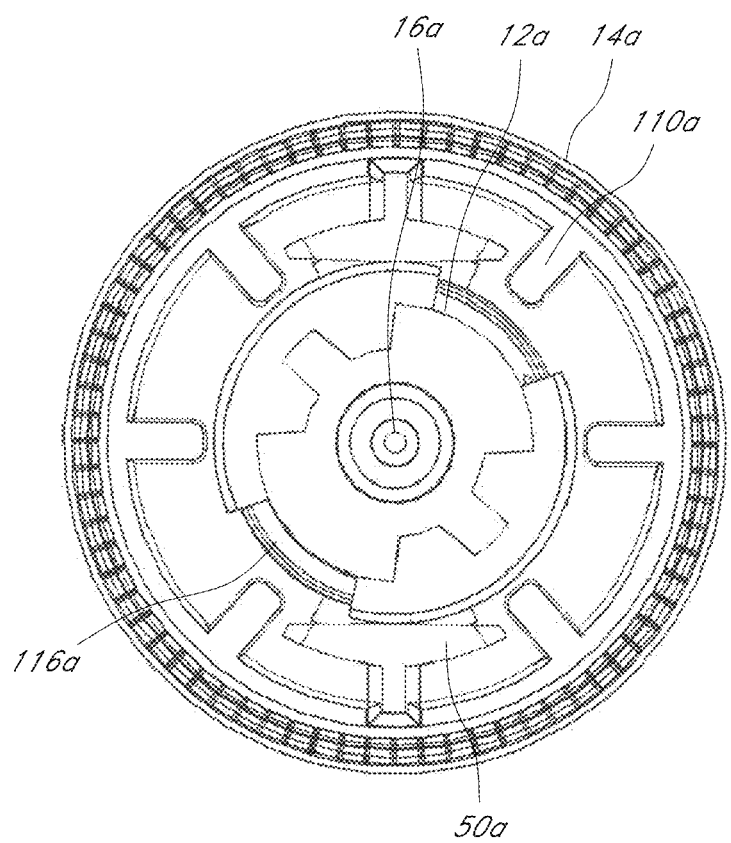
FIG. 10B illustrates a cross-sectional view along the line 10B-10B.

Referring to FIGS. 10-10B, the cover 10a is shown in a partially retracted configuration. As discussed above, the guide member 44a travels proximally a distance along a first track 80a during retraction of the sleeve 12a. The guide member 44a can be directed into a transfer track 84a intersecting the first track 80a and in turn directed into a second track 82a, thereby at least partially rotating the sleeve 12a with respect to the housing 14a. The transfer track 84a can be inclined, such that a height difference exists between the transfer track 84a and the second track 82a. The incline in the transfer track 84a can produce a slight but noticeable resistance. The guide member 44a can be directed across the height difference and into the second track 82a, and can thereby produce an audible or tactile alert. The height difference can prevent or inhibit the guide member 44a from returning into the transfer track 84a and, in turn, inhibit rotation of the sleeve 12. In the arrangement shown, as the sleeve 12a rotates, an outwardly extending portion 100a of a flange 64a rotates into radial interference with the second end 54a.

Figure 11:
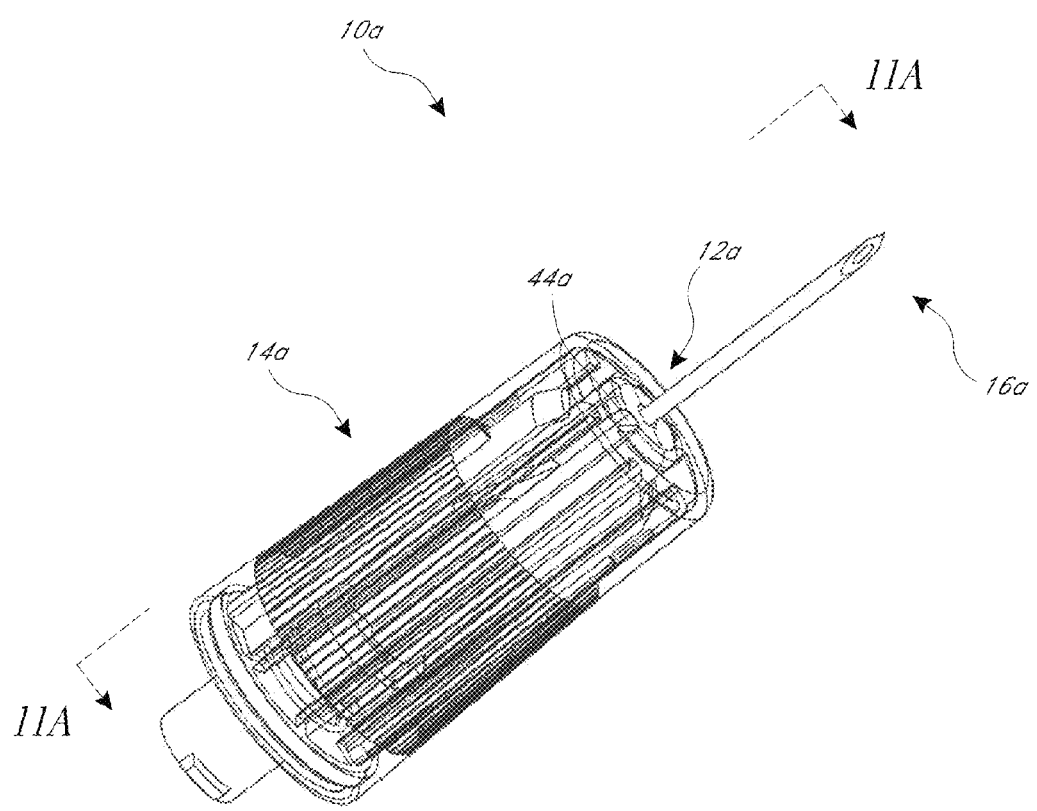
FIG. 11 illustrates a perspective view of the embodiment of FIG. 9 in a fully retracted second position.
Figure 11A:
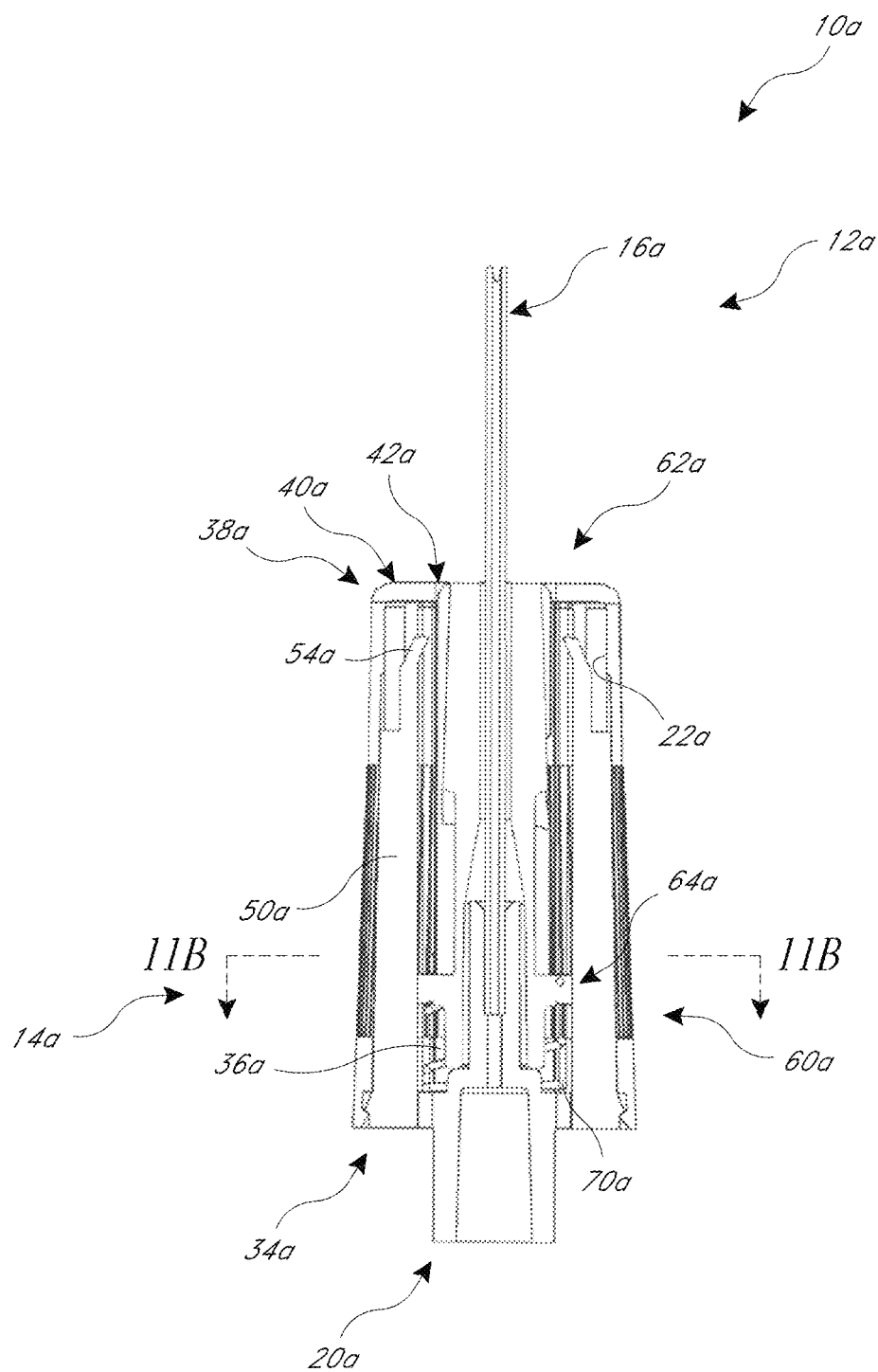
FIG. 11A illustrates a cross-sectional view along the line 11A-11A.
Figure 11B:
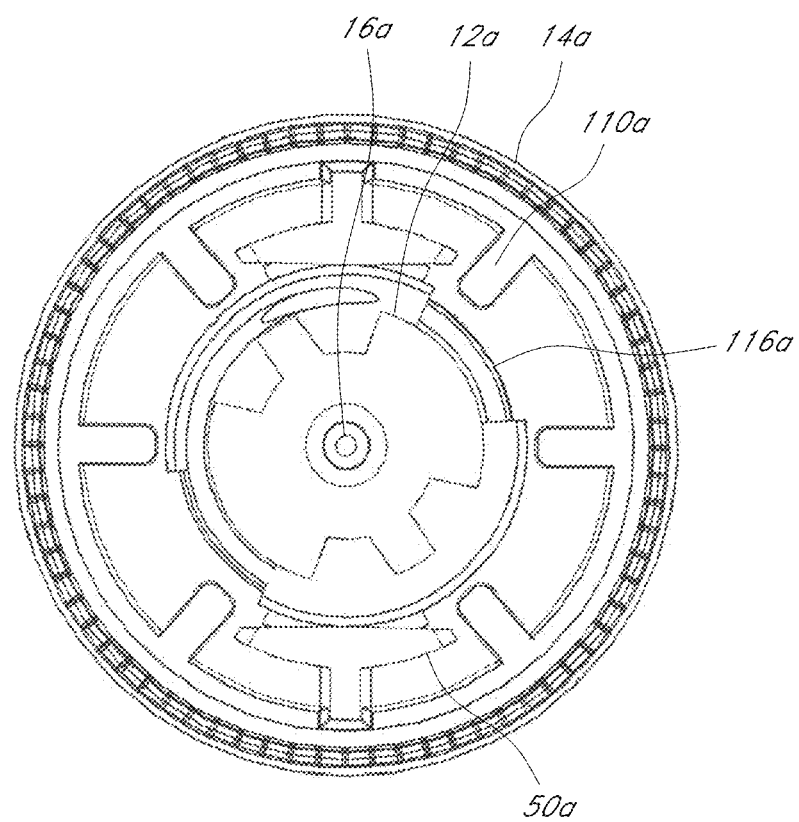
FIG. 11B illustrates a cross-sectional view along the line 11B-11B.
Figure 12:
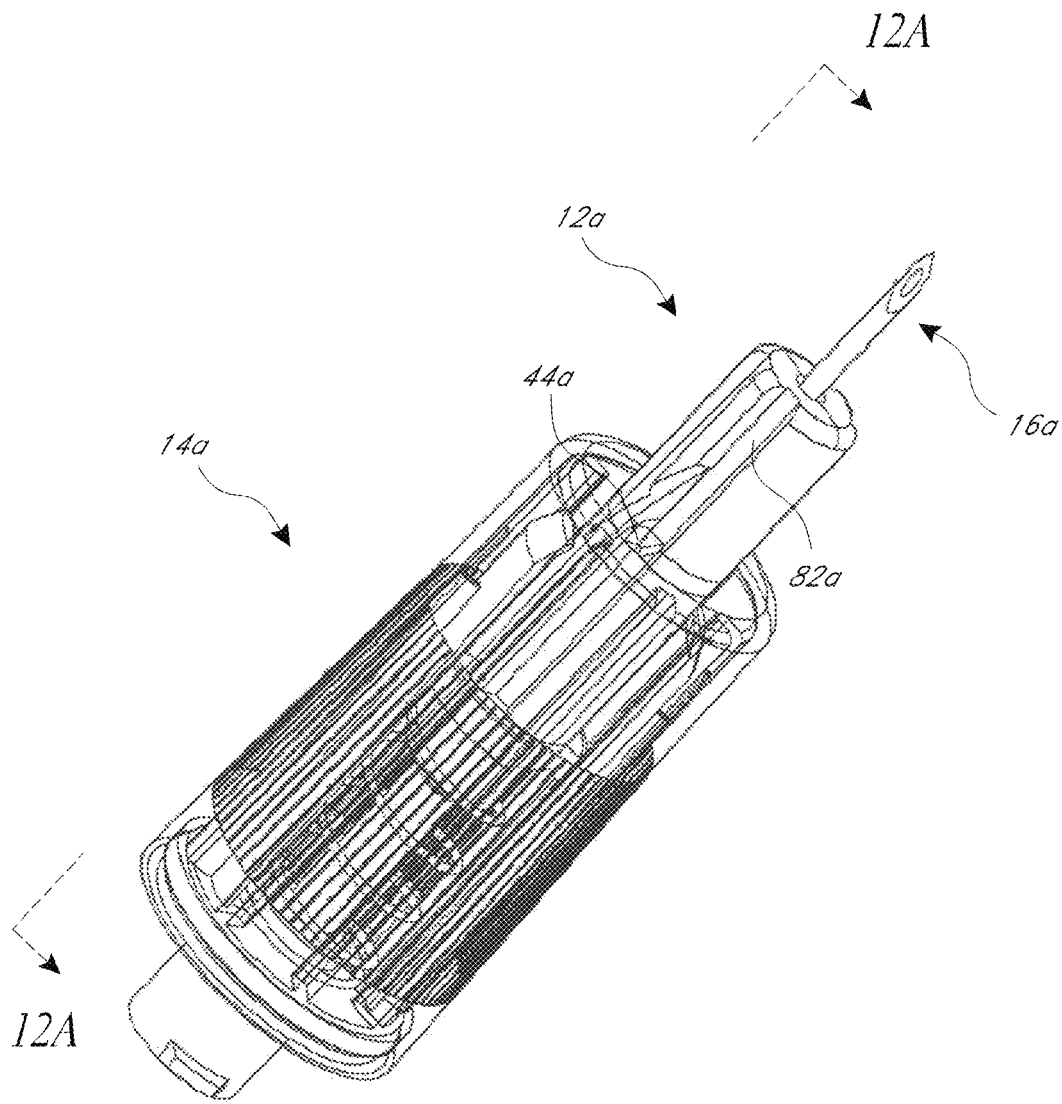
FIG. 12 illustrates a perspective view of the embodiment of FIG. 9 in a first partially extended position.
Figure 12A:
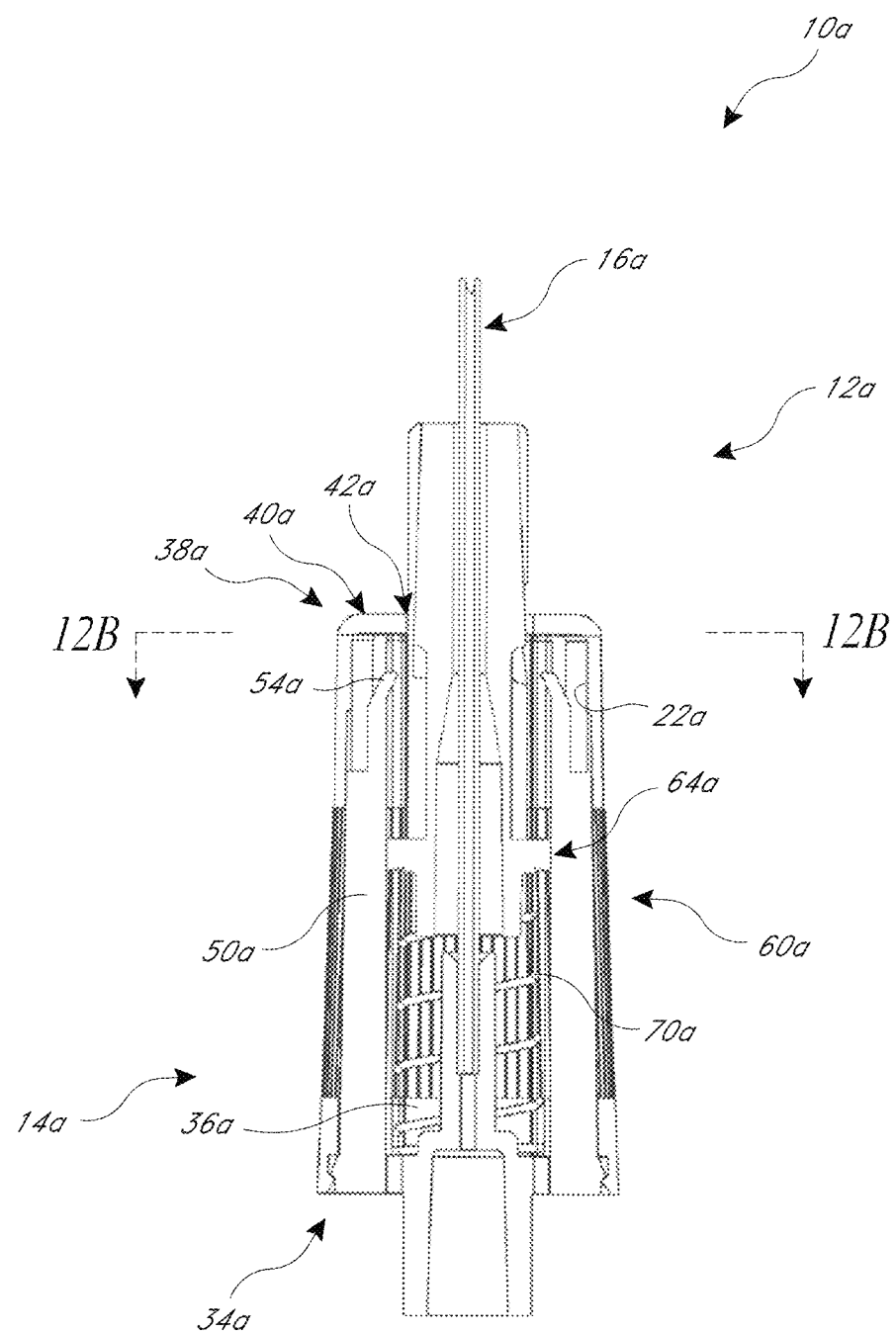
FIG. 12A illustrates a cross-sectional view along the line 12A-12A.
Figure 12B:
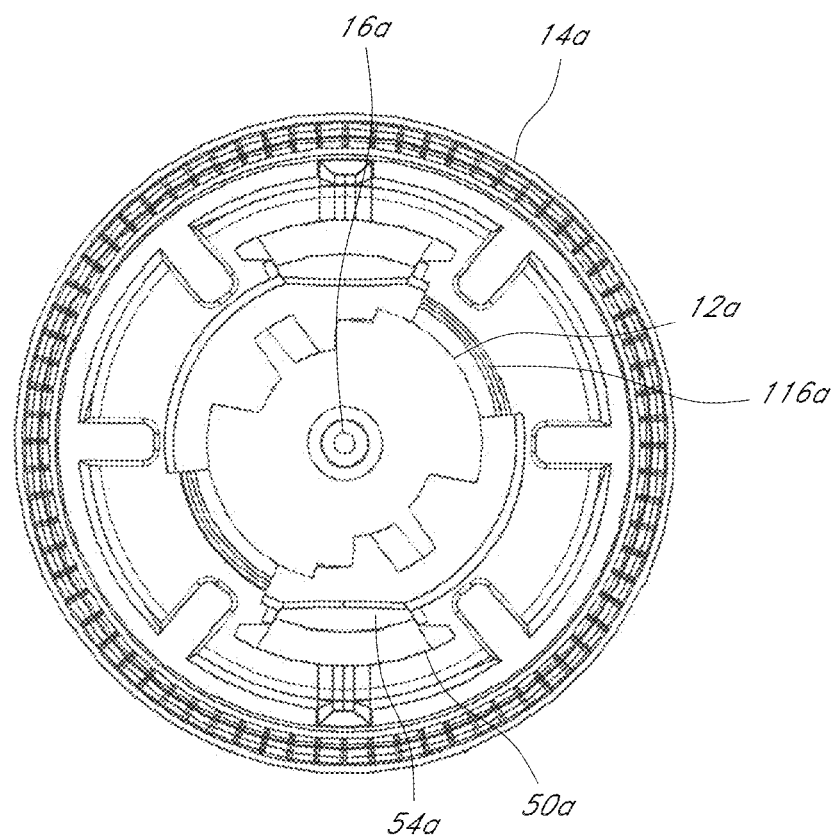
FIG. 12B illustrates a cross-sectional view along the line 12B-12B.
Figure 13:
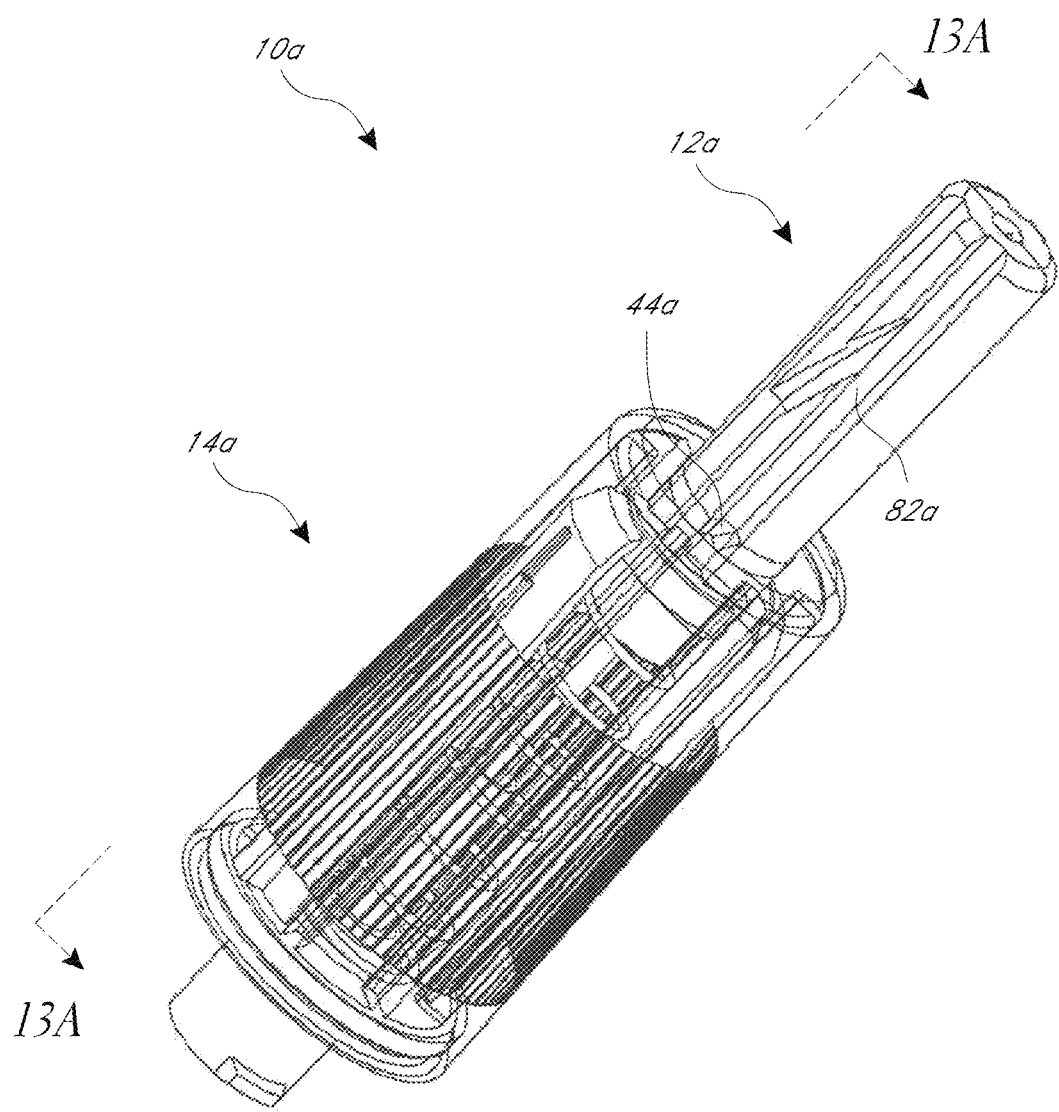
FIG. 13 illustrates a perspective view of the embodiment of FIG. 9 in a second partially extended position.
Figure 13A:
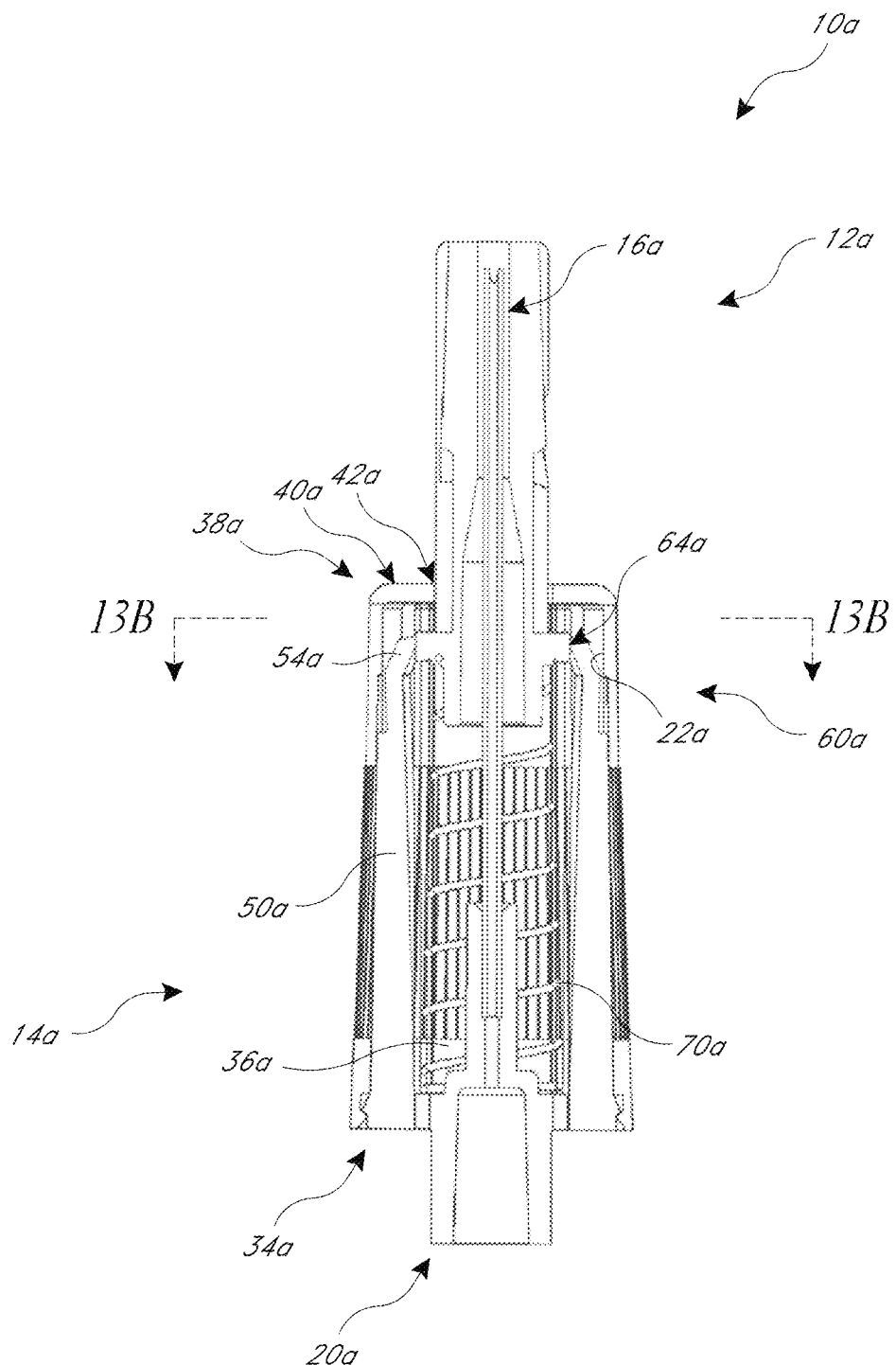
FIG. 13A illustrates a cross-sectional view along the line 13A-13A.
Figure 13B:
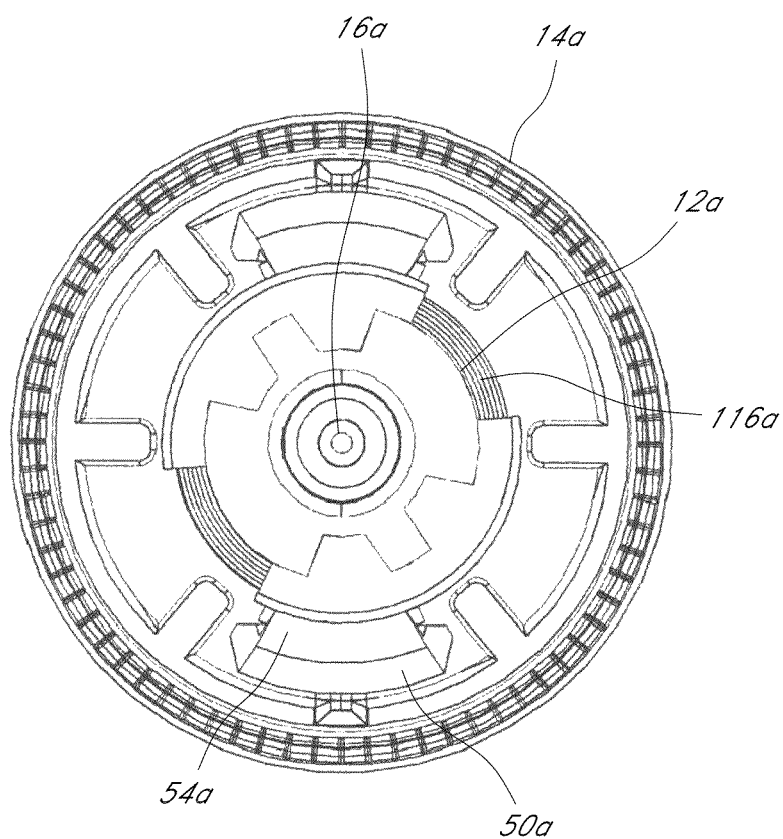
FIG. 13B illustrates a cross-sectional view along the line 13B-13B.

FIGS. 11 and 11A depict the cover 10a in a configuration with the sleeve 12a fully retracted. The guide member 44a has been directed into and traveled a distance along the second track 82a. As shown, a distal end 62a of the sleeve 12a is generally flush with a distal end 38a of the housing 14a.

Figure 14:
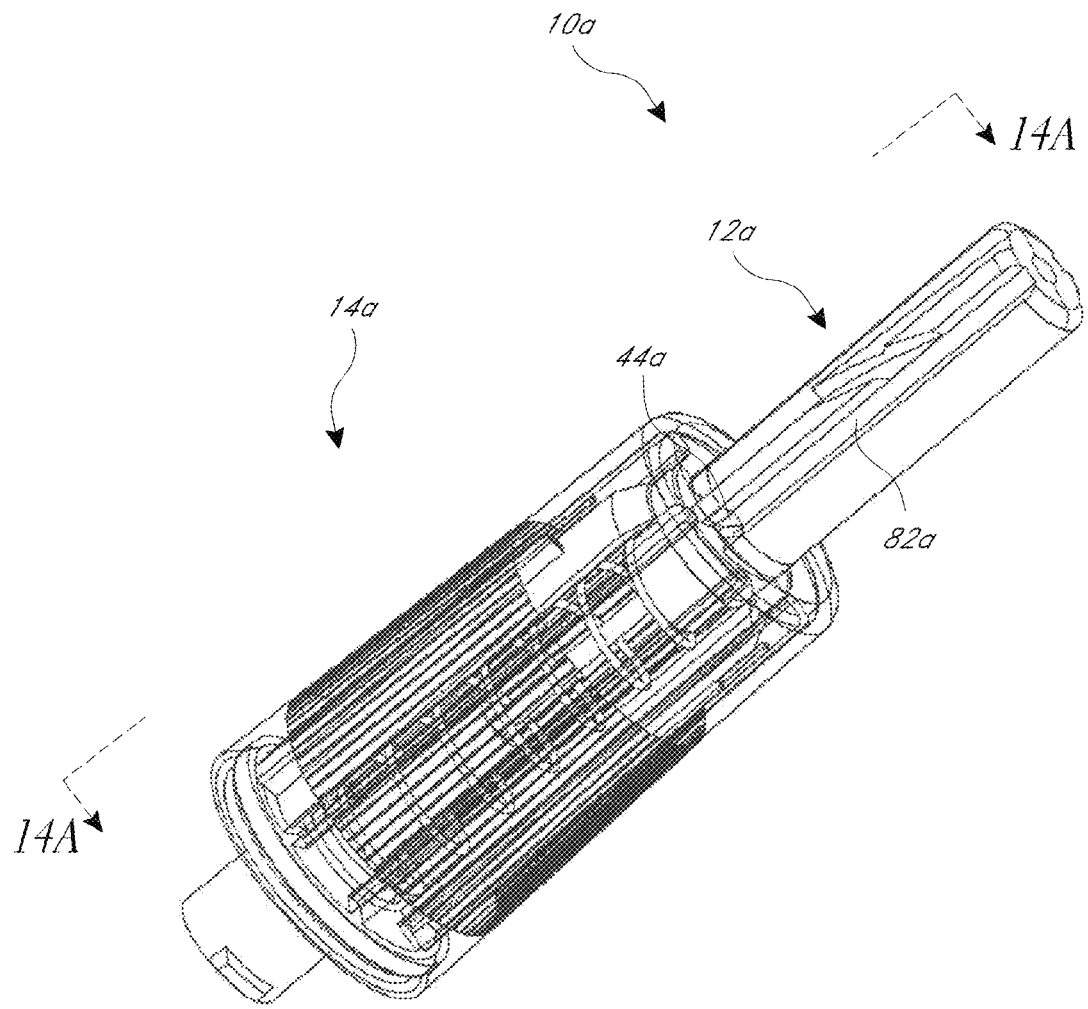
FIG. 14 illustrates a perspective view of the embodiment of FIG. 9 in a fully-extended, reuse-prevented, position.
Figure 14A:
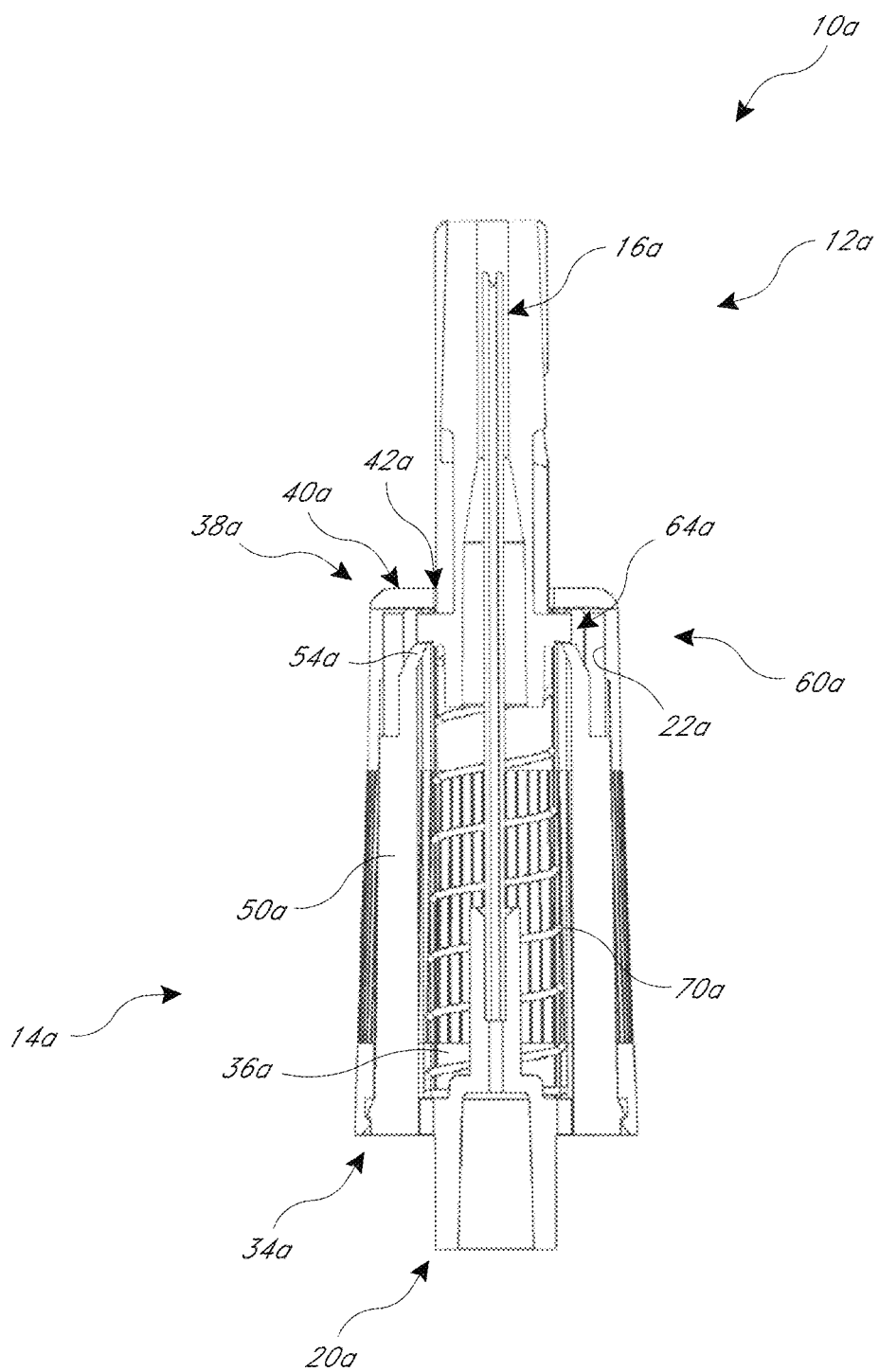
FIG. 14A illustrates a cross-sectional view along the line 14A-14A.

Configurations of the cover 10 with the sleeve 12a in progressively extended positions are shown in FIGS. 12-14A. As the bias of the spring 70a encourages the sleeve 12a distally, the guide member 44a in the second track 82a prevents or inhibits rotation of the sleeve 12a with respect to the housing 14a. As stated above, a height difference between the second track 82a and the transfer track 84a can prevent or inhibit the guide member 44a from moving from the second track 82a to the transfer track 84a. As the flange 64a nears the distal end 38a of the housing, the outwardly extending portion 100a encourages the axial locking member 50a radially outward, thereby producing a slight but noticeable resistance. Once the flange 64a has moved distal of the second end 54a of the axial locking member 50a, the locking member 50a returns radially inwardly to its position prior to engagement with the flange 64a. In several embodiments, such movement of the at axial locking member 50a produces a tactile or audible alert. As shown in FIG. 14A, the second end 54a of the at least one axial locking member 50a prevents the outwardly extending portion 100a of the flange 64a from moving proximally. Reuse of the cover 10a is therefore inhibited or prevented.

Although the needle cover has been disclosed in the context of certain preferred embodiments and examples, it will be understood by those skilled in the art that the needle cover extends beyond the specifically disclosed embodiments to other alternative embodiments and/or uses of the invention and obvious modifications and equivalents thereof. For example, the locking and/or reuse inhibiting features could be used in a variety of medical and non-medical fields. For example, although the embodiments of the sleeve and housing described above are generally circular in axial cross-sectional shape, other embodiments of the sleeve and housing employ various other shapes, such as square, elliptical, hexagonal, octagonal, or the like. It should be understood that various features and aspects of the disclosed embodiment can be combined with or substituted for one another in order to form varying modes of the needle cover. For example, in some embodiments the plurality of tracks are positioned on the inner surface of the housing and are configured to receive the guide member, which extends outwardly from the sleeve. Thus, it is intended that the scope of the needle cover herein-disclosed should not be limited by the particular disclosed embodiments described above, but should be determined only by a fair reading of the claims that follow.

The following is claimed:

1. An automatically locking needle cover comprising:
a housing configured to couple with a medical instrument, the housing comprising a locking member with an axial length;
a needle comprising a distal end and a proximal end; and
a sleeve that is slidably receivable within the housing and slidably movable over the needle, the sleeve comprising a flange with a notch, the sleeve being moveable relative to the housing and needle from an extended position to a retracted position to a locked position;
wherein:
in the extended position, the sleeve is circumferentially oriented relative to the housing such that the notch in the flange is substantially circumferentially aligned with the locking member;
in the course of movement of the sleeve from the extended position to the retracted position:
the flange moves proximally relative to the housing and the needle;
the locking member axially passes through the notch; and
the sleeve rotates relative to the housing such that the notch in the flange is out of circumferential alignment with the locking member;
in the retracted position, the distal end of the needle is exposed;
in the course of movement of the sleeve from the retracted position to the locked position:
the flange moves distally relative to the housing and the needle;
the flange deflects the locking member from an undeflected position to a deflected position; and
in response to the flange moving distally beyond the axial length of the locking member, the locking member resiliently returns to substantially the undeflected position; and
in the locked position:
a portion of the sleeve extends distal of the distal end of the needle and inhibits access to the distal end of the needle; and
the locking member provides a physical interference to proximal movement of the sleeve relative to the housing and the needle, thereby inhibiting the distal end of the needle from being reexposed.

2. The automatically locking needle cover of claim 1, wherein a distal tip of the sleeve comprises stimulation features configured to engage the skin of a patient prior to a distal tip of the needle contacting the skin of the patient, whereby the stimulation features reduce pain by stimulating the patient's pressure-receptor nerves.

3. The automatically locking needle cover of claim 2, wherein the stimulation features comprise a plurality of bumps.

4. The automatically locking needle cover of claim 1, wherein the flange deflects the locking member radially outwardly.

5. The automatically locking needle cover of claim 1, wherein:
the housing comprises a plurality of locking members and the flange of the sleeve comprises a corresponding plurality of notches; and
in the extended position, the sleeve is circumferentially oriented relative to the housing such that the each of the notches is substantially circumferentially aligned with a corresponding one of the locking members.

6. The automatically locking needle cover of claim 1, wherein, in the course of movement of the sleeve from the extended position to the retracted position, the flange engages a second locking member, the second locking member configured to facilitate substantially one-way rotation of the sleeve relative to the housing.

7. The automatically locking needle cover of claim 1, wherein the locking member comprises an arm with a distal end and a proximal end, the distal end of the arm being positioned radially inward of the proximal end of the arm when the sleeve is in the extended and locked positions.

8. The automatically locking needle cover of claim 1, wherein the locking member comprises a means for axially locking the sleeve.

9. The automatically locking needle cover of claim 1, wherein the proximal end of the needle is secured with and contained in the housing.

10. The automatically locking needle cover of claim 1, wherein the needle is substantially completely obscured from view when the sleeve is in the extended position and the locked position.

11. The automatically locking needle cover of claim 1, wherein the housing further comprises a shoulder that provides a physical interference to distal movement of the sleeve relative to the housing and the needle when the sleeve is in the locked position.

12. The automatically locking needle cover of claim 1, further comprising a cam mechanism configured to convert a proximally-directed force applied to a distal tip of the sleeve into rotation and translation of the sleeve relative to the housing and the needle.

13. The automatically locking needle cover of claim 1, wherein the medical implement comprises a syringe.

14. A method of manufacturing an automatic locking needle cover having an axial axis, the method comprising:
  obtaining a proximal portion of a housing;
  obtaining a distal portion of the housing, the distal portion comprising a distal opening;
  obtaining a sleeve comprising a flange;
  wherein one of the sleeve and the distal portion of the housing comprise a guide member, and the other of the sleeve and the distal portion of the housing comprise first and second tracks that are substantially parallel with the axial axis, the first track comprising an insertion portion and a radially inclined portion;
  inserting the sleeve through the distal opening of the distal portion of the housing such that the guide member enters the insertion portion of the first track;
  sliding the guide member the axial length of the insertion portion of the first track;
  sliding the guide member up the radially inclined portion;
  sliding the guide member axially beyond the radially inclined portion, thereby moving the guide member out of the insertion portion of the first track;
  sliding the guide member in the first track a distance such that the guide member is proximal of, and axially spaced apart from, the radially inclined portion;
  engaging the sleeve with the distal portion of the housing, whereby the engagement inhibits further distal movement of the sleeve relative to the distal portion of the housing; and
  compressing a biasing member between the sleeve and the proximal portion of the housing, thereby energizing the biasing member and biasing the sleeve.

15. The method of claim 14, further comprising verifying that, when the sleeve is moved proximally relative to the housing:
  a stop portion of the first track inhibits the guide member from reentering the insertion portion; and
  the stop portion directs the guide member into a transfer track in the other of the sleeve and the distal portion of the housing.

16. The method of claim 15, further comprising verifying that, when the sleeve is moved further proximally relative to the housing, the guide portion exits the transfer track and enters the second track.

17. The method of claim 14, wherein the proximal and distal portions of the housing are separate components, and the method further comprises joining the proximal and distal portions.

18. The method of claim 14, further comprising securing a needle with the proximal portion of the housing.

19. The method of claim 14, wherein obtaining the proximal portion comprises molding the proximal portion, obtaining the distal portion comprises molding the distal portion, and obtaining the sleeve comprises molding the sleeve.

20. The method of claim 14, wherein engaging the sleeve with the distal portion of the housing comprises abutting the sleeve with the distal portion of the housing.

21. The method of claim 14, wherein the guide member moves relative to the second track.

* * * * *